US006433008B1

(12) United States Patent
Kelleher et al.

(10) Patent No.: US 6,433,008 B1
(45) Date of Patent: Aug. 13, 2002

(54) α-ARYL-N-ALKYLNITRONES AND PHARMACEUTICAL COMPOSITIONS CONTAINING THE SAME

(75) Inventors: Judith A. Kelleher, Fremont; Kirk R. Maples, San Jose; Alina Dykman, San Fransisco; Yong-Kang Zhang, San Jose; Allan L. Wilcox, Mountain View, all of CA (US); Julian Levell, Bridgewater, NJ (US)

(73) Assignee: Centaur Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/529,555

(22) Filed: Jul. 18, 2000

Related U.S. Application Data

(60) Provisional application No. 60/062,324, filed on Oct. 17, 1997, provisional application No. 60/063,736, filed on Oct. 29, 1997, and provisional application No. 60/090,475, filed on Jun. 24, 1998.

(51) Int. Cl.$^7$ .................................................. A61K 31/36
(52) U.S. Cl. ........................................................ 514/464
(58) Field of Search ........................................... 514/464

(56) References Cited

U.S. PATENT DOCUMENTS 6,046,232 A    4/2000   Kelleher et al. ............ 514/464

*Primary Examiner*—Amelia Owens
(74) *Attorney, Agent, or Firm*—Burns, Doane, Swecker & Mathis, LLP

(57) ABSTRACT

Disclosed are novel aryl-N-alkylnitrone compounds and pharmaceutical compositions containing such compounds. The disclosed compositions are useful as therapeutics for preventing and/or treating neurodegenerative, autoimmune and inflammatory conditions in mammals and as analytical reagents for detecting free radicals.

17 Claims, 1 Drawing Sheet

α-ARYL-N-ALKYLNITRONES AND PHARMACEUTICAL COMPOSITIONS CONTAINING THE SAME

CROSS-REFERENCE TO RELATED APPLICATIONS

This application claims the benefit of U.S. Provisional Application No. 60/062,324, filed Oct. 17, 1997; U.S. Provisional Application No. 60/063,736, filed Oct. 29, 1997; and U.S. Provisional Application No. 60/090,475, filed Jun. 24, 1998. These applications are incorporated herein by reference in their entirety.

BACKGROUND OF THE INVENTION

1. Field of the Invention

This invention relates to novel α-aryl-N-alkylnitrones and their use as therapeutic agents and analytical reagents. More particularly, this invention concerns novel α-aryl-N-alkylnitrones and their use as therapeutics for treating and/or preventing neurological, autoimmune and inflammatory conditions in mammals and as analytical reagents for detecting free radicals.

2. State of the Art

Alzheimer's disease is a neurodegenerative condition in which nerve cells in the brain are systematically destroyed resulting in progressive memory loss, mental confusion and ultimately death. The National Institute on Aging (NIA) has recently estimated that about 4 million people in the United States are currently afflicted with Alzheimer's disease. At present, there is no treatment that effectively prevents the disease or reverses its symptoms.

In recent years, significant progress has been made in understanding the pathogenesis of Alzheimer's disease. For example, it is now known that patients with Alzheimer's disease develop amyloid plaque deposits around and between the nerve cells of their brain. These plaque deposits are made up of fibrillar aggregates of a small peptide called amyloid β-peptide or Aβ. The plaque deposits initially form in the hippocampus and cortical regions of the brain (areas associated with memory and cognition) and then spread to other areas as the disease progresses. The deposition of fibrils and plaques is also followed by inflammation of the surrounding support cells, called glia, which may lead to further loss of neurons. Eventually, the nerve cells in the brains of most Alzheimer's patients develop tangles of a microtubule-associated protein, called tau, which are believed to be a response by the nerve cells to damage.

Progress in understanding the underlying mechanisms of Alzheimer's disease has led to the development of various in vitro and in vivo models to identify compounds effective for preventing and/or treating Alzheimer's disease and other neurodegenerative conditions. In one such in vitro model, compounds are evaluated for their ability to intervene in Aβ(1-40) or Aβ(1-42) beta-pleated sheet formnation. Since the deposition of amyloid β-peptide is associated with the development of Alzheimer's disease, compounds which effectively disrupt the formation of Aβ(1-40) beta-pleated sheets are potentially useful for preventing and/or reversing Alzheimer's disease-related amyloid deposits.

In another in vitro model, compounds are evaluated for their ability to protect against Aβ(25-35)-induced neuronal cell loss in rat embryonic hippocampal neuronal/astrocyte cultures. As discussed above, patients with Alzheimer's disease suffer a progressive loss of neuronal cells. Accordingly, compounds which are effective in this in vitro test are potentially useful for reducing or preventing neuronal cell loss in patients afflicted with Alzheimer's disease or other neurodegenerative conditions.

A third in vitro Alzheimer's disease model is based on the observation that β-amyloid increases the release of cytokines, such as interleukin-1β (IL-1β), interleukin-6 (IL-6) and tumor necrosis factor-α (TNFα), in human monocyte cells induced with lipopolysaceharide (LPS). IL-1β, IL-6 and TNFα are proteins associated with inflammatory and immune responses. As previously mentioned, the deposition of fibrils in the brains of Alzheimer's patients is associated with inflammation of the surrounding support cells. See, S. D. Yan et al., *Proc. Natl. Acad. Sci. USA.* 94, 5296 (1997). Thus, compounds effective in this in vitro test are potentially useful for reducing and/or preventing the inflammation associated with Alzheimer's disease.

Additionally, elevated levels of IL-1β, IL-6. TNFα and other cytokines are associated with a wide variety of inflammatory and autoimmune conditions, including septic shock, rheumatoid arthritis, erythema nodosum leprosy, meningococcal meningitis, multiple sclerosis, systemic lupus and the like. See, L. Sekut et al., *Drug News Perspect.* 1196, 9, 261; and A. Waage et al., *J. Exp. Med.* 1989, 170, 1859–1867. Accordingly, compounds which inhibit the production of such cytokines are potentially useful for treating such inflammatory and autoimimune conditions.

Similarly, various in vivo disease models are available for identifying compounds useful for preventing and/or treating neurodegenerative, autoimmnune and inflammatory conditions. One such in vivo disease model is based on the observation that mammals suffer cognitive impairment when Aβ(25-35) and ibotenate are injected into the hippocampus of their brain. Since amyloid β-peptide deposits are associated with Alzheimer's disease, compounds which effectively reduce the cognitive impairment caused by Aβ(25-35)/ibotenate are potentially useful for the prevention and/or treatment of Alzheimer's disease and other neurodegenerative conditions. Another in vivo disease model is based on the observation that certain strains of autoimmune mice develop cognitive deficits as they mature. See, for example, Forster et al., *Behav. Neural Biology* 1988, 49, 139–151. Thus, compounds which prevent or reduce such cognitive deficits are potentially useful for preventing and/or treating neurodegenerative and autoimmune conditions.

It has now been discovered that certain novel α-aryl-N-alkylnitrone compounds effectively inhibit the formation of Aβ(1-42) beta-pleated sheets and/or protect against neuronal cell loss and/or inhibit the release of cytokines, such as IL-1β and TNFα. Additionally, in in vivo tests, these compounds have been found to reduce the cognitive impairment caused by Aβ(25-35)/ibotenate and to reduce the cognitive deficits that develop in certain strains of autoimmune mice. Accordingly, such compounds are useful for the prevention and/or treatment of neurodegenerative, autoimmune and inflammatory conditions in mammals.

The α-aryl-N-alkylnitrone compounds of this invention are also useful as analytical reagents for detecting free radicals. In this regard, the compounds of this invention function as "spin traps" by reacting with unstable free radicals to form relatively stable free radical spin adducts which are observable by electron spin resonance (ESR) spectroscopy. Accordingly, when used as spin traps, the compounds of this invention allow free radicals to be identified and studied using ESR and related techniques.

SUMMARY OF THE INVENTION

This invention provides novel α-aryl-N-alkylnitrone compounds which are useful as therapeutics for treating and/or preventing neurological, autoimmune and inflammatory conditions in mammals and as analytical reagents for detecting free radicals. In particular, the compounds of this invention are useful for preventing and/or treating Alzheimer's disease.

Accordingly, in one of its composition aspects, this invention is directed to compounds of formula I:

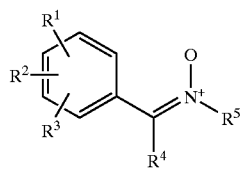

I wherein
- $R^1$ is selected from the group consisting of alkoxy, alkaryloxy, alkcycloalkoxy, aryloxy, and cycloalkoxy;
- $R^2$ is selected from the group consisting of hydrogen, alkoxy, alkcycloalkoxy, cycloalkoxy and halogen, or when $R^1$ and $R^2$ are attached to adjacent carbon atoms, $R^1$ and $R^2$ may be joined together to form an alkylenedioxy group;
- $R^3$ is selected from the group consisting of hydrogen, alkoxy, alkcycloalkoxy, cycloalkoxy and halogen;
- $R^4$ is selected from the group consisting of hydrogen and alkyl;
- $R^5$ is selected from the group consisting of alkyl having at least 3 carbon atoms, substituted alkyl having at least 3 carbon atoms and cycloalkyl;
  provided that:
  (i) when $R^2$ and $R^3$ are independently hydrogen or methoxy, $R^1$ is not methoxy;
  (ii) when $R^2$, $R^3$ and $R^4$ are hydrogen and $R^5$ is tert-butyl, then $R^1$ is not 4-n-butoxy, 4-n-pentyloxy or 4-n-hexyloxy;
  (iii) when $R^2$, $R^3$ and $R^4$ are hydrogen and $R^5$ is isopropyl, then $R^1$ is not 4-ethoxy;
  (iv) when $R^1$ and $R^2$ are joined together to form a 3,4-methylenedioxy group and $R^3$ and $R^4$ are hydrogen, then $R^5$ is not isopropyl or tert-butyl;
  (v) when $R^2$, $R^3$ and $R^4$ are hydrogen and $R^5$ is 1-hydroxy-2-methylprop-2-yl, then $R^1$ is not 2-ethoxy;
  (vi) when $R^1$ is 4-methoxy, $R^2$ is 3-ethoxy, and $R^3$ and $R^4$ are hydrogen, then $R^5$ is not 2,2-dimethylbut-3-yl or 1-hydroxy-2-methylprop-2-yl; and
  (vii) when $R^3$ and $R^4$ are hydrogen and $R^5$ is tert-butyl, then $R^1$ is not 4-methoxy when $R^2$ is 2-fluoro, and $R^1$ is not 2-methoxy when $R^2$ is 4-fluoro.

Preferably, in the compounds of formula I above, $R^1$ is selected from the group consisting of alkoxy, alkaryloxy and cycloalkoxy. More preferably, $R^1$ is alkoxy having 1 to about 8 carbon atoms or alkaryloxy having 7 to about 10 carbon atoms. Particularly preferred $R^1$ groups include methoxy, ethoxy, butoxy, pentyloxy, hexyloxy, cyclohexyloxy, heptyloxy, octyloxy, benzyloxy, 4-fluorobenzyloxy and 4-methoxybenzyloxy.

$R^2$ is preferably selected from the group consisting of hydrogen, alkoxy and fluoro. More preferably, $R^2$ is hydrogen, alkoxy having 2 to about 8 carbon atoms, or fluoro. Particularly preferred $R^2$ groups include hydrogen, ethoxy and fluoro.

When $R^1$ and $R^2$ are attached to adjacent carbon atoms, $R^1$ and $R^2$ are also preferably joined together to form an alkylenedioxy group having 1 to about 6 carbon atoms. Particularly preferred alkylenedioxy groups include methylenedioxy and ethylenedioxy, provided that when $R^1$ and $R^2$ are joined together to form a 3,4-methylenedioxy group and $R^3$ and $R^4$ are hydrogen, then $R^5$ is not isopropyl or tert-butyl.

Preferably, $R^3$ is hydrogen or alkoxy. More preferably, $R^3$ is hydrogen or alkoxy having 2 to 8 carbon atoms. Particularly preferred $R^3$ groups include hydrogen and ethoxy.

$R^4$ is preferably hydrogen or lower alkyl. More preferably, $R^4$ is hydrogen or alkyl having 1 to 4 carbon atoms. Still more preferably, $R^4$ is hydrogen.

$R^5$ is preferably selected from the group consisting of alkyl having 3 to about 8 carbon atoms, substituted alkyl having 3 to 8 carbon atoms and cycloalkyl having 3 to about 10 carbon atoms. More preferably, $R^5$ is alkyl having 3 to 6 carbon atoms or cycloalkyl having 5 to 6 carbon atoms.

Particularly preferred $R^5$ groups include n-propyl, isopropyl, 1-methoxy2-methylproo-2-yl, n-butyl, but-2-yl, tert-butyl, 2-methylbut-2-yl, 3-methylbut-1-yl, 3,3-dimethylbut-2-yl, 4-methylpent-2-yl, 2,4-dimethyl-2-pentyl, 2,2,4,4-tetramethylpent-3-yl, cyclopropyl, cyclobutyl, tert-octyl (2,4,4-trimethylpent-2-yl), cyclopentyl, cyclohexyl, cyclooctyl, 1-adamantyl, 2-adamantyl, 3,5-dimethyl-1-adamantyl and benzyl. When $R^5$ is adamantyl, 1-adamantyl is preferred.

Other suitable $R^5$ groups include, by way of example, 1-phenylethyl, 1-phenylprop-2-yl, 2-phenylprop-2-yl, 2-benzylprop-2-yl, 2-(methoxycarbonyl)prop-2-yl, 1,3-dihydroxy-2-(hydroxymethyl)prop-2-yl, 1-sulfo-2-methylprop-2-yl, 4-fluorobenzyl, 3,4-dimethoxybenzyl, 3-thiomethoxybut-1-yl and 3-thiomethoxyprop-1-yl.

An especially preferred group of compounds of formula I are those in which $R^1$ is a 2-ethoxy group; $R^2$, $R^3$ and $R^4$ are each hydrogen; and $R^5$ is as defined above.

Another especially preferred group of compounds of formula I are those in which $R^1$ is a 4-ethoxy group; $R^2$, $R^3$ and $R^4$ are each hydrogen; and $R^5$ is as defined above.

Still another especially preferred group of compounds of formula I are those in which $R^1$ is a 4-benzyloxy group; $R^2$, $R^3$ and $R^4$ are each hydrogen; and $R^5$ is as defined above.

Yet another especially preferred group of compounds of formula I are those in which $R^1$ is a 3-ethoxy group; $R^2$ is a 4-methoxy group; $R^3$ and $R^4$ are each hydrogen; and $R^5$ is as defined above.

In a preferred embodiment, this invention is directed to a compound of formula II:

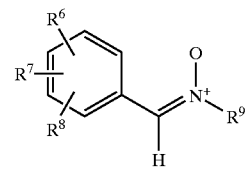

II wherein
- $R^6$ is selected from the group consisting of alkoxy having 1 to 8 carbon atoms, alkaryloxy having 7 to 10 carbon atoms, aryloxy having 6 to 10 carbon atoms and cycloalkoxy having 3 to 10 carbon atoms;
- $R^7$ is selected from the group consisting of alkoxy having 1 to 8 carbon atoms and fluoro, or when $R^6$ and $R^7$ are attached to adjacent carbon atoms, $R^6$ and $R^7$ may be joined together to form an alkylenedioxy group having 1 to about 6 carbon atoms;
- $R^8$ is selected from the group consisting of hydrogen and alkoxy having 1 to 8 carbon atoms; and $R^9$ is selected from the group consisting of alkyl having 3 to about 8 carbon atoms, substituted alkyl having 3 to about 8 carbon atoms and cycloalkyl having 3 to about 10 carbon atoms;
provided that:
(i) when $R^7$ is methoxy and $R^8$ is hydrogen or methoxy, $R^6$ is not methoxy;
(ii) when $R^6$ and $R^7$ are joined together to form a 3,4-methylenedioxy group and $R^8$ is hydrogen, then $R^9$ is not isopropyl or tert-butyl; and
(iii) when $R^6$ is 4-methoxy, $R^7$ is 3-ethoxy and $R^8$ is hydrogen, then $R^9$ is not 2,2-dimethylbut-3-yl or 1-hydroxy-2-methylprop-2-yl.

In a preferred embodiment, $R^6$ is alkoxy having 1 to 8 carbon atoms, $R^7$ is alkoxy having 2 to 8 carbon atoms and $R^8$ is hydrogen. In this embodiment, particularly preferred $R^6$ groups include methoxy, ethoxy, butoxy, pentyloxy, hexyloxy, heptyloxy and octyloxy, and particularly preferred $R^7$ groups include ethoxy. More preferably, $R^6$ is methoxy and $R^7$ is ethoxy.

In another preferred embodiment, $R^6$ is ethoxy; and $R^7$ and $R^8$ are hydrogen.

In yet another preferred embodiment, $R^6$ is benzyloxy, $R^7$ is alkoxy having 1 to 8 carbon atoms, and $R^8$ is hydrogen. In this embodiment, particularly preferred $R^7$ groups include methoxy, ethoxy, butoxy, pentyloxy, hexyloxy, heptyloxy and octyloxy. In another preferred embodiment, $R^6$ is benzyloxy; and $R^7$ and $R^8$ are hydrogen.

In still another preferred embodiment, $R^6$ is alkoxy having 1 to 8 carbon atoms, $R^7$ is fluoro and $R^8$ is hydrogen. In this embodiment, particularly preferred $R^6$ groups include methoxy, ethoxy, butoxy, pentyloxy, hexyloxy, heptyloxy and octyloxy.

In yet another preferred embodiment, $R^6$ and $R^7$ are joined together to form a methylenedioxy or ethylenedioxy group and $R^8$ is hydrogen, provided that when $R^6$ and $R^7$ are joined together to form a 3,4-methylenedioxy group and $R^8$ is hydrogen, then $R^9$ is not isopropyl or tert-butyl.

In the above embodiments, $R^9$ is preferably alkyl having 3 to 6 carbon atoms or cycloalkyl having 5 to 10 carbon atoms. Particularly preferred $R^9$ groups include n-propyl, isopropyl, 1-methoxy2-methylproo-2-yl, n-butyl, but-2-yl, tert-butyl, 2-methylbut-2-yl, 3-methylbut-1-yl, 3,3-dimethylbut-2-yl, 4-methylpent-2-yl, 2,4-dimethyl-2-pentyl, 2,2,4,4-tetramethylpent-3-yl, cyclopropyl, cyclobutyl, tert-octyl (2,4,4-trimethylpent-2-yl), cyclopentyl, cyclohexyl, cyclooctyl, 1-adamantyl, 2-adamantyl, 3,5-dimethyl-1-adamantyl, benzyl. When $R^9$ is adamantyl, 1-admantyl is preferred. Especially preferred $R^9$ groups are isopropyl, tert-butyl, 2,4-dimethyl-2-pentyl, tert-octyl, 1-adamantyl, cyclopropyl and cyclohexyl.

In another of its composition aspects, this invention is directed to each of the individual compounds:

α-(4-heptyloxyphenyl)-N-tert-butylnitrone
α-(4-hexyloxyphenyl)-N-n-propylnitrone
α-(3-ethoxy4-methoxyphenyl)-N-tert-butylnitrone
α-(4-ethoxyphenyl)-N-tert-butylnitrone
α-(4-benzyloxy-3-methoxyphenyl)-N-tert-butyinitrone
α-[3-(4-methoxyphenoxy)phenyl]-N-tert-butylnitrone
α-(2-ethoxyphenyl)-N-tert-butylnitrone
α-(3,4-ethylenedioxyphenyl)-N-tert-butylnitrone
α-(4-ethoxyphenyl)-N-cyclohexylnitrone
α-(4-benzyloxy-3-methoxyphenyl)-N-cyclohexylnitrone
α-(3-ethoxy-4-methoxyphenyl)-N-cyclohexylnitrone
α-(3,4-ethylenedioxyphenyl)-N-yclohexylnitrone
α-(4-ethoxy-3-methoxyphenyl)-N-cyclohexylnitrone
α-(3,4-ethylenedioxyphenyl)-N-isopropylnitrone
α-(3-ethoxy4-methoxyphenyl)-N-isopropylnitrone
α-(2-ethoxyphenyl)-N-isopropylnitrone
α-(2-ethoxyphenyl)-N-cyclohexylnitrone
α-(4-benzyloxy-3-methoxyphenyl)-N-isopropylnitrone
α-(4-ethoxy-3-methoxyphenyl)-N-isopropyinitrone
α-(3-ethoxy-4-hexyloxyphenyl)-N-cyclohexylnitrone
α-(4-benzyloxy-3-methoxyphenyl)-N-n-butylnitrone
α-(4-ethoxy-3-methoxyphenyl)-N-n-butylnitrone
α-(2-ethoxyphenyl)-N-n-butyinitrone
α-(3-ethoxy-4-methoxyphenyl)-N-n-butyinitrone
α-(3-ethoxy-4-hexyloxyphenyl)-N-isopropylnitrone
α-(3-ethoxy-4-hexyloxyphenyl)-N-tert-butylnitrone
α-(2-fluoro-4-octyloxyphenyl)-N-tert-butylnitrone
α-(2,4,6-triethoxyphenyl)-N-tert-butylnitrone
α-(2,4,6-triethoxyphenyl)-N-cyclohexylnitrone
α-(2-n-butoxyphenyl)-N-tert-butylnitrone
α-(3,4-diethoxyphenyl)-N-tert-butylnitrone
α-(2-fluoro-4-heptyloxyphenyl)-N-tert-butylnitrone
α-(2-fluoro-4-ethoxyphenyl)-N-tert-butylnitrone
α-(2-fluoro-4-ethoxyphenyl)-N-cyclohexylnitrone
α-(2-ethoxyphenyl)-N-1-adamantylnitrone
α-(3-ethoxy-4-methoxyphenyl)-N-1-adamantylnitrone
α-(4-ethoxyphenyl)-N-cyclopentylnitrone
α-(4-ethoxyphenyl)-N-tert-octylnitrone
α-(4-benzyloxyphenyl)-N-tert-butylnitrone
α-(4-benzyloxyphenyl)-N-cyclopentylnitrone
α-(4-benzyloxyphenyl)-N-cyclohexylnitrone
α-(2-ethoxyphenyl)-N-cyclopentylnitrone
α-(3-ethoxy-4-methoxyphenyl)-N-tert-octylnitrone
α-(3-ethoxy-4-methoxyphenyl)-N-(2,4-dimethyl-2-pentyl)nitrone
α-(4-ethoxyphenyl)-N-n-butylnitrone
α-(2-ethoxyphenyl)-N-benzylnitrone
α-(3-ethoxy-4-methoxyphenyl)-N-(2,2,4,4-tetramethylpent-3-yl)nitrone
α-(3-ethoxy-4-methoxyphenyl)-N-(4-methylpent-2-yl)nitrone
α-(3-ethoxy-4-methoxyphenyl)-N-but-2-ylnitrone
α-(2-ethoxyphenyl)-N-but-2-ylnitrone
α-[4-(4-fluorobenzyloxy)phenyl]-N-tert-butylnitrone
α-(3-ethoxy-4-methoxyphenyl)-N-cyclopentylnitrone
α-(3-ethoxy-4-methoxyphenyl)-N-n-propylnitrone
α-(4-benzyloxyphenyl)-N-n-propylnitrone
α-(4-benzyloxyphenyl)-N-isopropylnitrone
α-(3-ethoxy-4-methoxyphenyl)-N-(2-methylbut-2-yl)nitrone
α-(2-ethoxyphenyl)-N-(2-methylbut-2-yl)nitrone
α-(3-ethoxy-4-methoxyphenyl)-N-cyclooctylnitrone
α-(2-ethoxyphenyl)-N-cyclobutylnitrone
α-(3-ethoxy-4-methoxyphenyl)-N-cyclobutylnitrone
α-(4-benzyloxyphenyl )-N-cyclobutylnitrone
α-(4-benzyloxyphenyl)-N-tert-octylnitrone
α-[4-(4-fluorobenzyloxy)phenyl]-N-cyclohexylnitrone
α-(2-ethoxyphenyl)-N-tert-octylnitrone
α-[4-(4-fluorobenzyloxy)phenyl]-N-isopropylnitrone
α-(2-ethoxyphenyl)-N-cyclooctylnitrone
α-(4-benzyloxyphenyl)-N-cyclopropylnitrone
α-(3-ethoxy-4-methoxyphenyl)-N-cyclopropylnitrone
α-(4-benzyloxyphenyl)-N-cyclooctylnitrone
α-(3-ethoxy-4-methoxyphenyl)-N-(3,5-dimethyl-1-adamantyl)nitrone
α-(4-benzyloxyphenyl)-N-1-adamantylnitrone α-(3-ethoxy-4-methoxyphenyl)-N-(1-methoxy-2-methylprop-2-yl)nitrone
α-(4-benzyloxyphenyl)-N-2-adamantylnitrone
α-(4-ethoxyphenyl)-N-cyclooctylnitrone
α-(4-ethoxyphenyl)-N-1-adamantylnitrone
α-[4-(4-methoxybenzyloxy)phenyl]-N-tert-butylnitrone
α-(3-ethoxy-4-methoxyphenyl)-N-(3-methylbut-1-yl)nitrone
α-(3-ethoxy-4-methoxyphenyl)-N-cyclooctylnitrone, and
α-[4-(4-fluorobenzyloxy)phenyl]-N-cyclopentylnitrone.

Particularly preferred compounds include:

α-(2-ethoxyphenyl)-N-tert-butylnitrone
α-(2-ethoxyphenyl)-N-cyclohexylnitrone
α-(4-ethoxyphenyl)-N-cyclohexylnitrone
α-(4-benzyloxyphenyl)-N-tert-butylnitrone
α-(4-benzyloxyphenyl)-N-cyclopentylnitrone
α-(3-ethoxy-4-methoxyphenyl)-N-adamantylnitrone, and
α-(3-ethoxy-4-methoxyphenyl)-N-tert-octylnitrone.

In another of its composition aspects, this invention is directed to pharmaceutical compositions comprising a pharmaceutically acceptable carrier and a pharmaceutically effective amount of a compound of formula I:

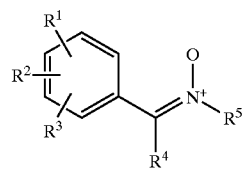

I wherein $R^1$–$R^5$ are as defined above.

In additional composition aspects, this invention is directed to pharmaceutical compositions comprising a pharmaceutically acceptable carrier and a pharmaceutically effective amount of a compound of formula II above.

As previously mentioned, the α-aryl-N-alkylnitrone compounds of this invention have been discovered to inhibit the formation of Aβ(1-42) beta-pleated sheets and/or to protect against Aβ(25-35)-induced neuronal cell loss and/or to reduce β-amyloid-induced release of cytokines, such as IL-1β and TNFα, in human monocyte cells. Such compounds have also been found to reduce the cognitive defects caused by Aβ(25-35)/ibotenate as well as those which develop in certain strains of autoimmune mice. Compounds having such properties are useful for preventing and/or treating neurodegenerative, autoimmune and inflammatory conditions.

Accordingly, in one of its method aspects, this invention is directed to a method for treating a patient with a neurodegenerative disease which method comprises administering to said patient a pharmaceutical composition comprising a pharmaceutically acceptable carrier and an effective neurodegenerative disease-treating amount of a compound of formula I or formula II above.

In another of its method aspects, this invention is directed to a method for preventing the onset of a neurodegenerative disease in a patient at risk for developing the neurodegenerative disease which method comprises administering to said patient a pharmaceutical composition comprising a pharmaceutically acceptable carrier and an effective neurodegenerative disease-preventing amount of a compound of formula I or formula II above.

In preferred embodiments of this invention, the neurodegenerative disease treated and/or prevented in the above methods is Alzheimer's disease, Parkinson's disease, HIV dementia and the like.

In still another of its method aspects, this invention is directed to a method for treating a patient with an autoimmune disease which method comprises administering to said patient a pharmaceutical composition comprising a pharmaceutically acceptable carrier and an effective autoimmune disease-treating amount of a compound of formula I or formula II above.

In yet another of its method aspects, this invention is directed to a method for preventing the onset of an autoimmune disease in a patient at risk for developing the autoimmune disease which method comprises administering to said patient a pharmaceutical composition comprising a pharmaceutically acceptable carrier and an effective autoimnmune disease-preventing amount of a compound of formula I or formula II above.

In preferred embodiments of this invention, the autoimmune disease treated and/or prevented in the above methods is systemic lupus, multiple sclerosis and the like.

In still another of its method aspects, this invention is directed to a method for treating a patient with an inflammatory disease which method comprises administering to said patient a pharmaceutical composition comprising a pharmaceutically acceptable carrier and an effective inflammatory disease-treating amount of a compound of formula I or formula II above.

In yet another of its method aspects, this invention is directed to a method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a compound of formula I or formula II above.

In preferred embodiments of this invention, the inflammatory disease treated and/or prevented in the above methods is rheumatoid arthritis, septic shock, erythema nodosum leprosy, septicemia, adult respiratory distress syndrome (ARDS), inflammatory bowel disease (IBD), uveitis and the like.

In another of its aspects, this invention is directed to the use of a compound of formula I or formula II above in the manufacture of a formulation or medicament for a medicinal treatment. Preferably, the medical treatment is the therapeutic or prophylactic treatment of a neurodegenerative disease, an autoimmune disease or an inflammatory disease.

Particularly preferred compounds include those represented in Tables I and II below.

TABLE I

| $R^a$ | $R^b$ | $R^c$ | $R^d$ |
|---|---|---|---|
| H— | H— | CH₃(CH₂)₆—O— | (CH₃)₃C— |
| H— | H— | CH₃(CH₂)₅—O— | CH₃CH₂CH₂— |
| H— | CH₃CH₂—O— | CH₃—O— | (CH₃)₃C— |
| H— | H— | CH₃CH₂—O— | (CH₃)₃C— |
| H— | CH₃—O— | PhCH₂—O— | (CH₃)₃C— |
| H— | 4-(CH₃—O)—Ph-O— | H— | (CH₃)₃C— |
| CH₃CH₂—O— | H— | H— | (CH₃)₃C— |
| H— | —O—CH₂CH₂—O— | | (CH₃)₃C— |
| H— | H— | CH₃CH₂—O— | cyclohexyl- |
| H— | CH₃—O— | PhCH₂—O— | cyclohexyl- |
| H— | CH₃CH₂—O— | CH₃—O— | cyclohexyl- |
| H— | —O—CH₂CH₂—O— | | cyclohexyl- |
| H— | CH₃—O— | CH₃CH₂—O— | cyclohexyl- |
| H— | —O—CH₂CH₂—O— | | (CH₃)₂CH— |
| H— | CH₃CH₂—O— | CH₃—O— | (CH₃)₂CH— |
| CH₃CH₂—O— | H— | H— | (CH₃)₂CH— |
| CH₃CH₂—O— | H— | H— | cyclohexyl- |
| H— | CH₃—O— | PhCH₂—O— | (CH₃)₂CH— |
| H— | CH₃—O— | CH₃CH₂—O— | (CH₃)₂CH— |
| H— | CH₃CH₂—O— | CH₃(CH₂)₅—O— | cyclohexyl- |
| H— | CH₃—O— | PhCH₂—O— | CH₃(CH₂)₃— |
| H— | CH₃—O— | CH₃CH₂—O— | CH₃(CH₂)₃— |
| CH₃CH₂—O— | H— | H— | CH₃(CH₂)₃— |
| H— | CH₃CH₂—O— | CH₃—O— | CH₃(CH₂)₃— |
| H— | CH₃CH₂—O— | CH₃(CH₂)₅—O— | (CH₃)₂CH— |
| H— | CH₃CH₂—O— | CH₃(CH₂)₅—O— | (CH₃)₃C— |
| F— | H— | CH₃(CH₂)₇—O— | (CH₃)₃C— |
| CH₃(CH₂)₃—O— | H— | H— | (CH₃)₃C— |
| H— | CH₃CH₂—O— | CH₃CH₂—O— | (CH₃)₃C— |
| F— | H— | CH₃(CH₂)₅—O— | (CH₃)₃C— |
| F— | H— | CH₃CH₂—O— | (CH₃)₃C— |
| F— | H— | CH₃CH₂—O— | cyclohexyl- |
| CH₃CH₂—O— | H— | H— | 1-adamantyl- |
| H— | CH₃CH₂—O— | CH₃—O— | 1-adamantyl- |
| H— | H— | CH₃CH₂—O— | cyclopentyl- |
| H— | H— | CH₃CH₂—O— | (CH₃)₃CCH₂—(CH₃)₂C— |
| H— | H— | PhCH₂—O— | (CH₃)₃C— |
| H— | H— | PhCH₂—O— | cyclopentyl- |
| H— | H— | PhCH₂—O— | cyclohexyl- |
| CH₃CH₂—O— | H— | H— | cyclopentyl- |
| H— | CH₃CH₂—O— | CH₃—O— | (CH₃)₃CCH₂—(CH₃)₂C— |
| H— | CH₃CH₂—O— | CH₃—O— | (CH₃)₂CHCH₂—(CH₃)₂C— |
| H— | H— | CH₃CH₂—O— | CH₃(CH₂)₃— |
| CH₃CH₂—O— | H— | H— | PhCH₂— |
| H— | CH₃CH₂—O— | CH₃—O— | [(CH₃)₃C]₂CH— |
| H— | CH₃CH₂—O— | CH₃—O— | (CH₃)₂CHCH₂—(CH₃)CH— |
| H— | CH₃CH₂—O— | CH₃—O— | CH₃CH₂(CH₃)—CH— |
| CH₃CH₂—O— | H— | H— | CH₃CH₂(CH₃)—CH— |
| H— | H— | 4-F—PhCH₂—O— | (CH₃)₃C— |
| H— | CH₃CH₂—O— | CH₃—O— | cyclopentyl- |
| H— | CH₃CH₂—O— | CH₃—O— | CH₃CH₂CH₂— |
| H— | H— | PhCH₂—O— | CH₃CH₂CH₂— |
| H— | H— | PhCH₂—O— | (CH₃)₂CH— |
| H— | CH₃CH₂—O— | CH₃—O— | CH₃CH₂(CH₃)₂C— |
| CH₃CH₂—O— | H— | H— | CH₃CH₂(CH₃)₂C— |
| H— | CH₃CH₂—O— | CH₃—O— | cyclooctyl- |
| CH₃CH₂—O— | H— | H— | cyclobutyl- |
| H— | CH₃CH₂—O— | CH₃—O— | cyclobutyl- |
| H— | H— | PhCH₂—O— | cyclobutyl- |
| H— | H— | PhCH₂—O— | (CH₃)₃CCH₂—(CH₃)₂C— |
| H— | H— | 4-F—PhCH₂—O— | cyclohexyl- |
| CH₃CH₂—O— | H— | H— | (CH₃)₃CCH₂—(CH₃)₂C— |
| H— | H— | 4-F—PhCH₂—O— | (CH₃)₂CH— |
| CH₃CH₂—O— | H— | H— | cyclooctyl- |
| H— | H— | PhCH₂—O— | cyclopropyl- |
| H— | CH₃CH₂—O— | CH₃—O— | 2-adamantyl- |

TABLE I-continued

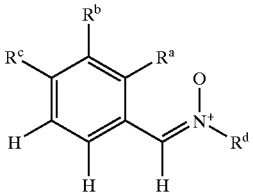

| $R^a$ | $R^b$ | $R^c$ | $R^d$ |
|---|---|---|---|
| H— | $CH_3CH_2$—O— | $CH_3$—O— | cyclopropyl- |
| H— | H— | $PhCH_2$—O— | cyclooctyl- |
| H— | $CH_3CH_2$—O— | $CH_3$—O— | 3,5-di($CH_3$)-1-adamantyl- |
| H— | H— | $PhCH_2$—O— | 1-adamantyl- |
| H— | $CH_3CH_2$—O— | $CH_3$—O— | $CH_3OCH_2$—$(CH_3)_2C$— |
| H— | H— | $PhCH_2$—O— | 2-adamantyl- |
| H— | H— | $CH_3CH_2$—O— | cyclooctyl- |
| H— | H— | $CH_3CH_2$—O— | 1-adamantyl- |
| H— | H— | 4-$CH_3O$—$PhCH_2$O— | $(CH_3)_3C$— |
| H— | $CH_3CH_2$—O— | $CH_3$—O— | $(CH_3)_2CHCH_2$—$CH_2$— |
| H— | $CH_3CH_2$—O— | $CH_3$—O— | cyclooctyl- |
| H— | H— | 4-F—$PhCH_2$—O— | cyclopentyl- |

TABLE II

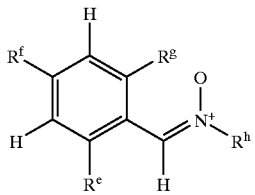

| $R^e$ | $R^f$ | $R^g$ | $R^h$ |
|---|---|---|---|
| $CH_3CH_2$—O— | $CH_3CH_2$—O— | $CH_3CH_2$—O— | $(CH_3)_3C$— |
| $CH_3CH_2$—O— | $CH_3CH_2$—O— | $CH_3CH_2$—O— | cyclohexyl- |

DETAILED DESCRIPTION OF THE INVENTION

Definitions

Figure 1:
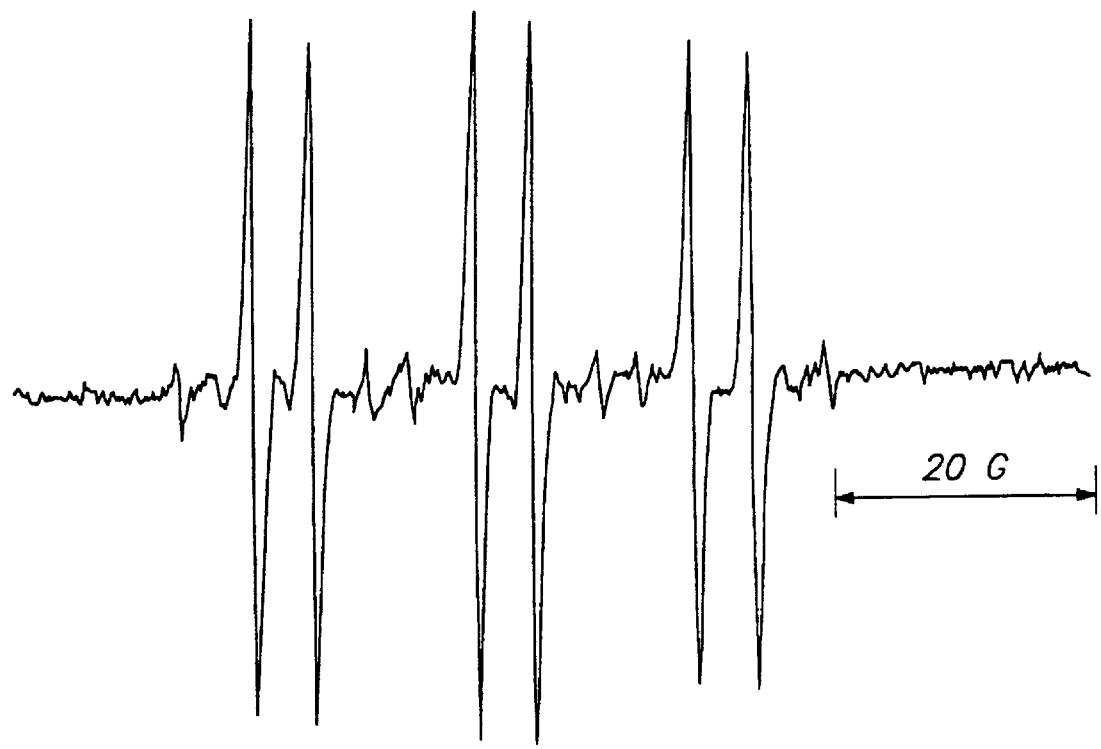
FIG. 1 is an electron spin resonance (ESR) spectra of the radical adduct of α-(2-ethoxyphenyl)-N-tert-butylnitrone and a methyl radical.

When describing the α-aryl-N-alkylnitrones, pharmaceutical compositions and methods of this invention, the following terms having the following meanings:

The term "β-amyloid peptide" refers to a 39–43 amino acid peptide having a molecular weight of about 4.2 kD, which peptide is substantially homologous to the form of the protein described by Glenner, et al., *Biochem. Biophys. Res. Commun.*, 120:885–890 (1984), including mutations and post-translational modifications of the normal β-amyloid peptide.

The term "cytokines" refers to peptide protein mediators that are produced by immune cells to modulate cellular functions. Examples of cytokines include, interleukin-1β (IL-1β), interleukin-6 (IL-6) and tumor necrosis factor-α (TNFα). "Acyl" refers to the group —OC(O)R where R is alkyl or aryl. "Alkyl" refers to monovalent alkyl groups preferably having from 1 to about 10 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to alkyl groups having 1 to 6 carbon atoms.

"Substituted alkyl" refers to an alkyl group, preferably of from 1 to 10 carbon atoms, having from 1 to 5 substituents, and preferably 1 to 3 substituents, selected from the group consisting of alkoxy, cycloalkyl, cycloalkoxy, acyl, aminoacyl, amino, aminocarbonyl, cyano, halogen, hydroxyl, carboxyl, keto, thioketo, alkoxycarbonyl, thiol, thioalkoxy, aryl, aryloxy, nitro, —$OSO_3H$ and pharmaceutically acceptable salts thereof, —SO-alkyl, —SO-substituted alkyl, —SO-aryl, —$SO_2$-alkyl, —$SO_2$-substituted alkyl, —$SO_2$-aryl, and mono- and di-alkylamino, mono- and di-arylamino, and unsymmetric di-substituted amines having different substituents selected from alkyl, substituted alkyl and aryl.

"Alkylene" refers to divalent alkylene groups preferably having from 1 to 10 carbon atoms and more preferably 1 to 6 carbon atoms which can be straight chain or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkylenedioxy" refers to —O-alkylene-O— groups preferably having from 1 to 10 carbon atoms and more preferably 1 to 6 carbon atoms which can be straight chain or branched. This term is exemplified by groups such as methylenedioxy (—$OCH_2O$—), ethylenedioxy (—$OCH_2CH_2O$—) and the like.

"Alkenylene" refers to divalent alkenylene groups preferably having from 2 to 10 carbon atoms and more preferably 2 to 6 carbon atoms which can be straight chain or branched and having at least 1 and preferably from 1–2 sites of alkenyl unsaturation. This term is exemplified by groups such as ethenylene (—CH=CH—), the propenylene isomers (e.g., —CH=$CHCH_2$— and —C($CH_3$)=CH— and —CH=C($CH_3$)—) and the like.

"Alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl, and the like.

"Alkaryloxy" refers to —O-alkylene-aryl groups preferably having from 1 to 10 carbon atoms in the alkylene moiety and from 6 to 14 carbon atoms in the aryl moiety. Such alkaryl groups are exemplified by benzyloxy, 4-fluorobenzyloxy, phenethyloxy, and the like.

"Alkcycloalkyl" refers to -alkylene-cycloalkyl groups preferably having from 1 to 10 carbon atoms in the alkylene moiety and from 3 to 8 carbon atoms in the cycloalkyl moiety. Such alkcycloalkyl groups are exemplified by —CH$_2$-cyclopropyl, —CH$_2$-cyclopentyl, —CH$_2$CH$_2$-cyclohexyl, and the like.

"Alkcycloalkoxy" refers to —O-alkylene-cycloalkyl groups preferably having from 1 to 10 carbon atoms in the alkylene moiety and from 3 to 8 carbon atoms in the cycloalkyl moiety. Such alkcycloalkoxy groups are exemplified by —OCH$_2$-cyclopropyl, —OCH$_2$-cyclopentyl, —OCH$_2$CH$_2$-cyclohexyl, and the like.

"Alkoxy" refers to the group "alkyl-O—". Preferred alkoxy groups include, by way of example, methoxy, ethoxy, n-propoxy, isopropoxy, n-butoxy, tert-butoxy, sec-butoxy, n-pentyloxy, n-hexyloxy, 1,2-dimethylbutoxy, and the like.

"Alkoxycarbonyl" refers to the group —C(O)OR where R is alkyl.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), isopropenyl (—C(CH$_3$)=CH$_2$), and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH$_2$C≡CH), and the like.

"Aminocarbonyl" refers to the group —C(O)NRR where each R is independently hydrogen or alkyl.

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 3 substituents selected from the group consisting of alkyl, alkoxy, alkaryloxy, alkenyl, alkynyl, amino, aminoacyl, aminocarbonyl, alkoxycarbonyl, aryl, carboxyl, cycloalkoxy, cyano, halo, hydroxy, nitro, trihalomethyl, thioalkoxy, and the like.

"Aryloxy" refers to —O-aryl groups wherein "aryl" is as defined above.

"Carboxyl" refers to the group —C(O)OH.

"Cyano" refers to the group —CN.

"Cycloalkyl" refers to cyclic alkyl groups of from 3 to 10 carbon atoms having a single cyclic ring or multiple condensed rings, including fused and bridged ring systems, which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkoxy" refers to —O-cycloalkyl groups. Such cycloalkoxy groups include, by way of example, cyclopentyloxy, cyclohexyloxy and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Halo" or "halogen" refers to fluoro, chloro, bromo and iodo. Preferred halo groups are either fluoro or chloro.

"Keto" or "oxo" refers to the group =O.

"Nitro" refers to the group —NO$_2$.

"tert-Octyl" refers to a 2,4,4-trimethyl-2-pentyl group.

"Thiol" refers to the group —SH.

"Thioalkoxy" refers to the group —S-alkyl.

"Thioketo" refers to the group =S.

"Pharmaceutically acceptable salt" refers to pharmaceutically acceptable salts which are derived from a variety of organic and inorganic counter-ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically acceptable cation" refers to a pharmaceutically acceptable cationic counter-ion of an acidic functional group. Such cations are exemplified by sodium, potassium, calcium, magnesium, ammonium, tetraalkylammonium cations, and the like.

General Synthetic Procedures

The α-aryl-N-alkylnitrones of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts. *Protecting Groups in Organic Synthesis*, Second Edition, Wiley, New York, 1991, and references cited therein.

In a preferred method of synthesis, the α-aryl-N-alkylnitrone compounds of this invention are prepared by coupling an aryl carbonyl compound of formula III:

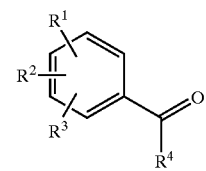

III wherein $R^1$–$R^4$ are as defined above, with a hydroxylamine of formula IV:

$$HO-NH-R^5 \qquad \qquad IV$$

wherein $R^5$ is as defined above, under conventional reaction conditions.

The coupling reaction is typically conducted by contacting the aryl carbonyl compound III with at least one equivalent, preferably about 1.1 to about 2 equivalents, of hydroxylamine IV in an inert polar solvent such as methanol, ethanol, 1,4-dioxane, tetrahydrofuran, dimethyl sulfoxide, dimethylformamide and the like. This reaction is preferably conducted at a temperature of from about 0° C. to about 100° C. for about 1 to about 48 hours. Optionally, a catalytic amount of an acid, such as hydrochloric acid, acetic acid, p-toluenesulfonic acid and the like, may be employed in this reaction. Upon completion of the reaction, the α-aryl-N-alkylnitrone of formula I is recovered by conventional methods including precipitation, chromatography, filtration, distillation and the like.

The aryl carbonyl compounds of formula III employed in the coupling reaction are either known compounds or compounds that can be prepared from known compounds by conventional procedures. For example, such compounds are readily prepared by acylation of the corresponding aryl compound with the appropriate acyl halide under Friedel-Crafts acylation reaction conditions. Additionally, the formyl compounds, i.e. those compounds where $R^4$ is hydrogen, can be prepared by formylation of the corresponding aryl compound using, for example, a disubstituted formamides, such as N-methyl-N-phenylformamide, and phosphorous oxychloride (the Vilsmeier-Haack reaction), or using $Zn(CN)_2$ followed by water (the Gatterman reaction). Numerous other methods are known in the art for preparing such aryl carbonyl compounds. Such methods are described, for example, in I. T. Harrison and S. Harrison, *Compendium of Organic Synthetic Methods*, Wiley, New York, 1971, and references cited therein.

Certain aryl carbonyl compounds of formula III can also be prepared by alkylation of the corresponding aryl hydroxy compound (e.g., 4-hydroxybenzaldehyde and the like). This reaction is typically conducted by contacting the aryl hydroxy compound with a suitable base, such as an alkali or alkaline earth metal hydroxide, fluoride or carbonate, in a inert solvent, such as ethanol. DMF and the like, to deprotonate the hydroxyl group. This reaction is generally conducted at about 0° C. to about 50° C. for about 0.25 to 2 hours. The resulting intermediate is then reacted in situ with about 1.0 to about 2.0 equivalents of an alkyl halide, preferably an alkyl bromide or iodide, at a temperature of from about 25° C. to about 100° C. for about 0.25 to about 3 days.

Additionally, various aryl aldehydes of formula III can be prepared by reduction of the corresponding aryl nitriles. This reaction is typically conducted by contacting the aryl nitrile with about 1.0 to 1.5 equivalents of a hydride reducing agent, such as $LiAlH(OEt)_3$, in an inert solvent such as diethyl ether, at a temperature ranging from about –78° to about 25° C. for about 1 to 6 hours. Standard work-up conditions using aqueous acid then provides the corresponding aryl aldehyde.

Preferred aryl carbonyl compounds include, but are not limited to, 2-ethoxybenzaldehyde, 4-ethoxybenzaldehyde, 2-butoxybenzaldehyde, 4-butoxybenzaldehyde, 4-pentyloxybenzaldehyde, 4-benzyloxybenzaldehyde, 4-(4-fluorobenzyloxy)benzaldehyde, 4-(4-methoxybenzyloxy) benzaldehyde, 4-hexyloxybenzaldehyde, 4-heptyloxybenzaldehyde, 3-ethoxy-4-methoxybenzaldehyde, 4-ethoxy-3-methoxybenzaldehyde, 3,4-diethoxybenzaldehyde, 3-ethoxy-4-hexyloxybenzaldehyde, 2-fluoro4-methoxybenzaldehyde, 2-fluoro-4-ethoxybenzaldehyde, 2-fluoro4-heptyloxybenzaldehyde, 2-fluoro-4-octyloxybenzaldehyde, 4-benzyloxy-3-methoxybenzaldehyde, 4-phenoxy-3-methoxybenzaldehyde, 3,4-methylenedioxybenzaldehyde (piperonal), 3,4-ethylenedioxybenzaldehyde, 2,4,6-triethoxybenzaldehyde, and the like.

The hydroxylamine compounds of formula V above are also known compounds or compounds which can be prepared from known compounds by conventional procedures. Typically, the hydroxylamine compounds of formula V are prepared by reduction of the corresponding nitro compound (i.e., $R^5$—$NO_2$, wherein $R^5$ is as defined above) using a suitable reducing agent such as activated zinc/acetic acid, activated zinclammnonium chloride or an aluminum/mercury amalgam. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc reagents or an ether/water mixture in the case of the aluminum amalgams. Aliphatic nitro compounds (in the form of their salts) can also be reduced to hydroxylamines using borane in tetrahydrofuran. Since some hydroxylamines have limited stability, such compounds are generally prepared immediately prior to reaction with the aryl carbonyl compound of formula III.

Preferred hydroxylamines for use in this invention include, but are not limited to, N-cyclopentylhydroxyamine, N-tert-octylhydroxyamine, N-tert-butylhydroxylamine, N-isopropylhydroxylamine, N-n-propylhydroxylamine, N-n-butylhydroxylamine, N-tert-butylhydroxylamine, N-cyclohexylhydroxylamine, N-2,4-dimethyl-2-pentylhydroxylamine, 1-adamantylhydroxylamine and the like.

Pharmaceutical Compositions

When employed as pharmaceuticals, the a-aryl-N-alkylnitrones of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the α-aryl-N-alkylnitrone compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the α-aryl-N-alkylnitrone compound in such compositions is typically a minor component, often being from about 0.05 to 10% by weight with the remainder being the injectable carrier and the like.

The above-described components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in the incorporated materials in *Remington's Pharmaceutical Sciences*.

The following formulation examples illustrate representative pharmaceutical compositions of this invention. The present invention, however, is not limited to the following pharmaceutical compositions.

FORMULATION 1-TABLETS

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active α-aryl-N-alkylnitrone compound per tablet) in a tablet press.

FORMULATION 2-CAPSULES

A compound of formula I is admixed as a dry powder with a starch diluent in an approximate 1:1 weight ratio. The mixture is filled into 250 mg capsules (125 mg of active α-aryl-N-alkylnitrone compound per capsule).

FORMULATION 3-LIQUID

A compound of formula 1 (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

FORMULATION 4-TABLETS

The compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active α-aryl-N-alkylnitrone compound) in a tablet press.

FORMULATION 5-INJECTION

The compound of formula I is dissolved in a buffered sterile saline injectable aqueous medium to a concentration of approximately 5 mg/ml.

Utility

The α-aryl-N-alkylnitrones of this invention have been discovered to inhibit the formation of Aβ(1-142) beta-pleated sheets and/or protect against neuronal cell loss and/or inhibit the release of cytokines, such as IL-1β and TNFα and/or protect against IL-1β/IFN$_\gamma$-induced toxicity. Additionally, such compounds have been found to reduce the cognitive deficits caused by Aβ(25-35)/ibotenate as well as those developed by certain autoimmune strains of mice. As previously discussed, the formation of Aβ(1-42) beta-pleated sheets, neuronal cell loss, beta amyloid-induced cognitive deficits are associated with neurodegenerative conditions, such as Alzheimer's disease, and/or autoimmune conditions. Additionally, elevated levels of cytokines are associated with neurodegenerative, autoimmune and/or inflammatory conditions. Accordingly, the compounds and pharmaceutical compositions of this invention find use as therapeutics for preventing and/or treating neurodegenerative, autoimmune and inflammatory conditions in mammals including humans.

Surprisingly, it has also been discovered that the dimethoxy and trimethoxy analogs of the compounds of formula I (i.e., compounds in which $R^1$ and $R^2$ are methoxy and $R^3$ is hydrogen or $R^1$, $R^2$ and $R^3$ are all methoxy) have significantly higher toxicity than the α-aryl-N-alkylnitrone compounds of formula I. Due to their toxicity, such di- and trimethoxy compounds are not useful as therapeutic agents or as analytical reagents for detecting free radicals in living biological systems.

Among the conditions which may be treated and/or prevented with the α-aryl-N-alkylnitrones of formula I are neurodegenerative conditions, such as Alzheimer's disease, Parkinson's disease, HIV-dementia and the like; autoimmune conditions, such as systemic lupus, multiple sclerosis and the like; and inflammatory conditions, such as inflammatory bowel disease (IBD), rheumatoid arthritis, septic shock, erythema nodosum leprosy, septicemia, uveitis, adult respiratory distress syndrome (ARDS) and the like.

Additionally, since the α-aryl-N-alkylnitrones of this invention have been discovered to effectively inhibit the release of cytokines, such a IL-1β, IL-6 and TNFα, such compounds are useful for treating diseases characterized by an overproduction or a dysregulated production of cytokines, particularly IL-1β, IL-6 and TNFα, including many autoimmune and/or inflammatory conditions.

As discussed above, the compounds described herein are suitable for use in a variety of drug delivery systems.

Injection dose levels for treating neurodegenerative, autoimmune and inflammatory conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of the α-aryl-N-alkylnitrone, with preferred doses each providing from about 0.1 to about 10 mg/kg and especially about 1 to about 5 mg/kg.

When used to prevent the onset of a neurodegenerative, autoimnmune or inflammatory condition, the α-aryl-N-alkylnitrones of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active α-aryl-N-alkylnitrone derivatives.

The novel α-aryl-N-alkylnitrones of this invention are also useful as analytical reagents, i.e. as spin traps, for detecting unstable free radicals using electron spin resonance (ESR) spectroscopy and related techniques. When used as analytical reagents, the nitrone compounds of this invention are typically contacted with the radical to be studied in solution and an ESR spectrum generated in a conventional manner. In particular, the α-aryl-N-alkylnitrones of this invention may be used to detect and identify free radicals in biological systems. Any ESR spectrometer, such as a JEOL JES-FE3XG spectrometer, may be employed in these experiments. Typically, the solution containing the spin-trap will be deoxygenated by, for example, bubbling argon or nitrogen through the solution before the ESR experiment is conducted. Preferably, an excess of the α-aryl-N-alkylnitrone is used in such ESR experiments.

The actual experimental procedures employed in the spin-trapping experiment will depend on a number of factors, such as the manner of radical production, the inertness of the solvent and reagents with respect to the spin trap, the lifetime of the spin adduct and the like. Spin trapping procedures are well known in the art and the exact procedure employed can be determined by those skilled in the art. Typical procedures and apparatus for conducting spin trapping experiments are described, for example, in C. A. Evans, "Spin Trapping", *Aldrichimica Acta*, (1979), 12(2), 23–29, and references cited therein.

The following synthetic and biological examples are offered to illustrate this invention and are not to be construed in any way as limiting the scope of this invention.

EXAMPLES

In the examples below, the following abbreviations have the following meanings. Abbreviations not defined below have their generally accepted meaning.

| | |
|---|---|
| bd = | broad doublet |
| bs = | broad singlet |
| d = | doublet |
| dd = | doublet of doublets |
| dec = | decomposed |
| $dH_2O$ = | distilled water |
| ELISA = | enzyme-linked immuno-sorbent assay |
| EtOAc = | ethyl acetate |
| EtOH = | ethanol |
| FBS = | fetal bovine serum |
| g = | grams |
| h = | hours |
| Hz = | hertz |
| IL-1β = | interleukin-1β |
| IL-6 = | interleukin-6 |
| L = | liter |
| LPS = | lipopolysaccharide |
| m = | multiplet |
| min = | minutes |
| M = | molar |
| MeOH = | methanol |
| mg = | milligram |
| MHz = | megahertz |
| mL = | milliliter |
| mmol = | millimole |
| m.p. = | melting point |
| N = | normal |
| q = | quartet |
| quint. = | quintet |
| s = | singlet |
| t = | triplet |
| THF = | tetrahydrofuran |
| ThT = | thioflavin T |
| tlc = | thin layer chromatography |
| TNFα = | tumor necrosis factor-α |
| μg = | microgram |
| μL = | microliter |
| UV = | ultraviolet |

In the examples below, all temperatures are in degrees Celsius (unless otherwise indicated). Example A–C describe the synthesis of intermediates useful for preparing α-aryl-N-alkylnitrones. The remaining examples describe the synthesis of α-aryl-N-alkylnitrones of this invention and comparative α-aryl-N-alkylnitrones, and the ESR, in vitro and in vivo testing of such compounds.

Example A

Synthesis of N-tert-Butylhydroxylamine

Zinc dust (648 g) was added in portions to a cooled mixture of 2-methyl-2-nitropropane (503 g) and ammonium chloride (207 g) in deionized water (6 L) at such a rate so as to maintain the temperature below 18° C. The reaction mixture was stirred mechanically for 15 hours and then filtered. The solid was washed with hot water (1.75 L). The combined filtrate was saturated with potassium carbonate (4.6 Kg) and extracted with ethyl acetate (2×1300 mL). The organic solution was dried over anhydrous sodium sulfate, filtered and rotary evaporated to give the title compound (329 g, 75.7% yield) as white crystals. This material was used without further purification.

Spectroscopic data were as follows:

$^1$H NMR (CDCl$_3$, 270 MHz) δ=1.090 (s, 3 CH$_3$).

Example B

Synthesis of N-Isopropylhydroxylamine

Using the procedure of Example A above and 1-methyl-1-nitroethane, the title compound was prepared. The crude hydroxylamine product was used without further purification.

Example C

Synthesis of N-Cyclohexylhydroxylamine

Using the procedure of Example A above and 1-nitrocyclohexane, the title compound can be prepared. Alternatively, N-cyclohexylhydroxylamine hydrochloride may be purchased commercially from Aldrich Chemical Company, Inc., Milwaukee, Wis. USA and neutralized with a base, such as potassium carbonate, to provide the title compound.

Example 1

Synthesis of α-(4-Heptyloxyphenyl)-N-tert-butylnitrone

The title compound was prepared according to the procedure described in Example 2 using 4-hydroxybenzaldehyde, 1-iodoheptane and 2-methyl-2-nitropropane. The title compound was isolated in 60% overall yield as a solid, m.p. 68.5° C.

Spectroscopic data were as follows:

IR (KBr, cm$^{-1}$): 3076.8 (CH), 2972.3 (CH), 1601.9 (C=N), 1250.9 (C—O—C) and 1118.8 (N—O).

$^1$H NMR (CDCl$_3$, 270 MHz) δ=8.25 (2H, d, J=8.9 Hz, phenyl 2H), 7.44 (1H, s, nitronyl H), 6.90 (2H, d, J=8.9 Hz, phenyl 2H), 3.98 (2H, t, J=6.7 Hz, CH$_2$), 1.77 (2H, quintet, J=6.7 Hz, CH$_2$), 1.58 (9H, s, 3 CH$_3$), 1.36 (8H, m, 4 CH$_2$) and 0.87 (3H, t, J=6.7 Hz, CH$_3$).

$^{13}$C NMR (CDCl$_3$, 67.9 MHz) δ=160.9, 131.0, 129.8, 124.0, 114.4, 69.9, 68.0, 31.5, 28.9, 28.7, 28.0, 25.6, 22.3 and 13.7.

Example 2

Synthesis of α-(4-Hexyloxyphenyl)-N-n-propylnitrone

A solution of 4-hydroxybenzaldehyde (27.11 g, 0.222 moles) in ethanol was refluxed with sodium hydroxide (8.88 g, 0.222 moles) for 30 minutes, 1-Iodohexane (47.10 g, 0.222 moles) was added in one portion and the solution refluxed for 68 hours. The ethanol was removed by rotary evaporation and the residue was reacted with 1-nitropropane, ammonium chloride, and zinc dust in H$_2$O/ethanol (300:20, v:v) for 18 hours at room temperature. The reaction mixture was filtered, the solvent removed by rotary evaporation, and the residue purified by column chromatography using ethyl acetate/hexane (1:1, v:v) as the eluant (R$_f$=0.42 on a silica gel plate using ethyl acetate/hexane (1:1, v:v) as the eluant). The title compound was isolated as a solid (1.63 g, 12.4% overall yield), m.p. 45° C.

Spectroscopic data was as follows:

$^1$H NMR (CDCl$_3$, 270 MHz): δ=8.22 (2H, d, J=8.8 Hz, phenyl 2H), 7.28 (1H, s, nitronyl H), 6.92 (2H, d, J=8.8 Hz, phenyl 2H), 3.93 (4H, m, 2CH$_2$), 2.07 (4H, m, CH$_2$), 1.36 (6H, m, 3CH$_2$), 1.00 (3H, t, CH$_3$), 0.908 (3H, t, CH$_3$).

Examples 3–6

Using the procedures described herein, the following compounds were prepared:

α-(3-Ethoxy-4-methoxyphenyl)-N-tert-butylnitrone
α-(4-Ethoxyphenyl)-N-tert-butylnitrone
α-(4-Benzyloxy-3-methoxyphenyl)-N-tert-butylnitrone, and
α-[3-(4-Methoxyphenoxy)phenyl]-N-tert-butylnitrone.

Example 7

Synthesis of α-(2-Ethoxyphenyl)-N-tert-butylnitrone

2-Ethoxybenzaldehyde (12.0 g, 79.90 mmol) and N-tert-butylhydroxylamine (10.69 g, 119.86 mmol) were mixed in chloroform with molecular sieves (50 g, 4 A) and silica gel (10 g). The mixture was sealed under argon gas and stirred for 70 h at room temperature. The mixture was then filtered and the solid washed with ethyl acetate and the combined solution was rotary evaporated. Pentane (50 mL) was added to the liquid residue and isolation of the resulting solid afforded 13.79 g (78.0% yield) of the title compound as white crystals, m.p. 58.3° C. (R$_f$=0.55 on a silica gel plate using ethyl acetate as the eluant).

Spectroscopic data were as follows:

IR (KBr, cm$^{-1}$): 2976.7 (CH), 2935 (CH), 1597.0 (C=N), 1567.1 (benzene ring) and 1123.6 (N—O).

$^1$H NMR (CDCl$_3$, 270 MHz): δ=9.322 (1H, dd, J$_1$=1.7 Hz, J$_2$=7.9 Hz, phenyl H), 8.067 (1H, s, CH=N), 7.302 (1H, td, J$_t$=7.9 Hz, J$_d$=1.7 Hz, phenyl H), 6.979 (1H, td, J$_t$=7.9 Hz, J$_d$=0.5 Hz, phenyl H), 6.839 (1H, d, J=7.9 Hz, phenyl H), 4.055 (2H, q, J=6.9 Hz, OCH$_2$), 1.586 (9H, s, 3 CH$_3$) and 1.423 (3H, t, J=6.9 Hz, CH$_3$).

$^{13}$C NMR (CDCl$_3$, 67.9 MHz): δ=156.948, 131.323, 128.836, 124.688, 120.813, 120.386, 110.868, 70.767, 63.842, 27.997 and 14.375.

Examples 8–10

Using the procedures described herein, the following compounds were prepared:

α-(3,4-Ethylenedioxyphenyl)-N-tert-butylnitrone, and
α-(3,4-Methylenedioxyphenyl)-N-tert-butylnitrone.
α-(4-ethoxyphenyl)-N-n-butylnitrone

Example 11

Synthesis of α-(4-Ethoxyphenyl)-N-cyclohexylnitrone

A solution of 4-ethoxybenzaldehyde (6.62 g, 44.1 mmol) in 200 mL of benzene was refluxed with N-cyclohexylhydroxylamine (6.61 g, 57.4 mmol) in the presence of p-toluenesulfonic acid (0.8 g, 4 mmol) for 72 h. After rotary evaporation, the residue was purified by recrystallization from hexanes and ethylene glycol dimethyl ether (100 mL, 3:1, v:v) to give the title compound (9.2 g, 84% yield) as a solid, m.p. 124.0° C.

Spectroscopic data were as follows:

IR (KBr, cm$^{-1}$): 2933.0, 2862 (CH), 1599.6 (C=N), 1297.0 (C—O—C) and 1149.4 (N—O).

$^1$H NMR (CDCl$_3$, 270 MHz): δ=8.20 (2H, d, J=8.9 Hz, phenyl 2H), 7.32 (1H, s, nitronyl H), 6.88 (2H, d, J=8.9 Hz, phenyl 2H), 4.05 (2H, quartet, J=7.0 Hz, CH$_2$), 3.75 (1H, m, CH), 1.94 (6H, m, 6 CH), 1.68 (2H, m, 2 CH), 1.39 (2H, t, J=7.0 Hz, CH$_3$) and 1.27 (2H, m, 2 CH).

$^{13}$C NMR (CDCl$_3$, 67.9 MHz): δ=160.6, 132.1, 130.7, 123.8, 114.4, 75.0, 63.4, 30.8, 24.7 and 14.3.

Example 12

Synthesis of α-(4-Benzyloxy-3-methoxyphenyl)-N-cyclohexylnitrone

The title compound was prepared according to the procedure described in Example 11 using 4-benzyloxy-3-methoxybenzaldehyde and N-cyclohexylhydroxylamine. The title compound was isolated in 97.9% yield as a solid, m.p. 154.1° C.

Spectroscopic data were as follows:

IR (KBr, cm$^{-1}$): 2935.3 (CH), 1595.4 (C=N), 1265.1 (C—O—C) and 1147.6 (N—O).

$^1$H NMR (CDCl$_3$, 270 MHz): δ=8.50 (1H, d, J=2.0 Hz, phenyl H), 7.34 (7H, m, phenyl H & nitronyl H), 6.86 (1H, d, J=8.4 Hz, phenyl H), 5.19 (2H, s, CH$_2$), 3.94 (3H, s, CH$_3$), 3.78 (1H, m, cyclohexyl H), 1.95 (6H, m, 6 cyclohexyl H), 1.67 (2H, m, 2 CH) and 1.30 (2H, m, 2 CH).

$^{13}$C NMR (CDCl$_3$, 67.9 MHz): δ=150.0, 149.4, 137.0, 132.5, 128.8, 128.2, 127.4, 124.8, 122.9, 113.3, 111.6, 75.2, 70.7, 55.7, 30.8 and 24.7.

Example 13

Synthesis of α-(3-Ethoxy-4-methoxyphenyl)-N-cyclohexylnitrone

The title compound was prepared according to the procedure described in Example 11 using 3-ethoxy-4-methoxybenzaldehyde and N-cyclohexylhydroxylamine. The title compound was isolated in 57% yield as a solid, m.p. 113.5° C.

Spectroscopic data were as follows:

IR (KBr, cm$^{-1}$): 2857.3 (CH), 1590.8 (C=N), 1265.0, 1239.0 (C—O—) and 1126.1 (N—O).

$^1$H NMR (CDCl$_3$, 270 MHz): δ=8.42 (1H, d, J=1.8 Hz, phenyl H), 7.39 (1H, dd, J=7.5 and 1.8 Hz, phenyl H), 7.32 (1H, s, nitronyl H), 6.84 (1H, d, J=7.5 Hz, phenyl H), 4.14 (2H, quartet, J=7.0 Hz, CH$_2$), 3.88 (3H, s, CH$_3$), 3.76 (1H, m, CH), 1.96 (6H, m, 6 CH), 1.68 (1H, m, CH), 1.44 (3H, t, J=7.0 Hz, CH$_3$) and 1.27 (3H, m, 3 CH).

$^{13}$C NMR (CDCl$_3$, 67.9 MHz): δ=150.95, 148.13, 132.47, 124.32, 122.93, 112.36, 110.91, 75.14, 64.10, 55.71, 30.80, 24.75 and 14.34.

Example 14

Synthesis of α-(3,4-Ethylenedioxyphenyl)-N-cyclohexylnitrone

The title compound was prepared according to the procedure described in Example 11 using 3,4-ethylenedioxybenzaldehyde and N-cyclohexylhydroxylamine. The title compound was isolated in 74.5% yield as a solid, m.p. 96.7° C.

Spectroscopic data were as follows:

IR (KBr, cm$^{-1}$): 2927.9 (CH), 1575.6 (C=N), 1319.5 (C—O—) and 1133.9 (N—O).

$^1$H NMR (CDCl$_3$, 270 MHz): δ=7.98 (1H, d, J=2.0 Hz, phenyl H), 7.60 (1H, dd, J=7.4 & 2.0 Hz, phenyl H), 7.27 (1H, s, nitronyl H), 6.83 (1H, d, J=7.4 Hz, phenyl H), 4.24 (4H, m, 2 CH$_2$), 3.75 (1H, m, CH), 1.94 (7H, m, 7 CH) and 1.28 (3H, m, 3 CH).

$^{13}$C NMR (CDCl$_3$, 67.9 MHz): δ=145.45, 143.45, 131.86, 124.75, 122.98, 117.76, 117.26, 75.16, 64.50, 63.98, 30.80 and 24.73.

Example 15

Using the procedures described herein, the following compound was prepared:

α-(4-Ethoxy-3-methoxyphenyl)-N-cyclohexylnitrone.

Example 16

Synthesis of α-(3,4-Ethylenedioxyphenyl)-N-isopropylnitrone

The title compound was prepared according to the procedure described in Example 11 using 3,4-ethylenedioxybenzaldehyde and N-isopropylhydroxylamine. The crude produce was purified by column chromatography over silica gel using ethyl acetate as the eluant. The title compound was isolated in 53% yield as a solid. m.p. 108.8° C. (R$_f$=0.31 on a silica gel plate using EtOAc as the eluant).

Spectroscopic data were as follows:

IR (KBr, cm$^{-1}$): 2978.9 (CH), 1582.3 (C=N), 1297.0 (C—O—) and 1063.8 (N—O).

$^1$H NMR (CDCl$_3$, 270 MHz): δ=7.99 (1H, d, J=2.0 Hz, phenyl H), 7.61 (1H, dd, J=8.5 & 2.0 Hz, phenyl H), 7.28 (1H, s, nitronyl H), 6.84 (1H, d, J=8.5 Hz, phenyl H), 4.25 (4H, m, 2 CH$_2$), 4.13 (1H, septet, J=6.7 Hz, CH) and 1.46 (6H, d, J=6.7 Hz, 2 CH$_3$).

$^{13}$C NMR (CDCl$_3$, 67.9 MHz): δ=145.5, 143.5, 131.6, 124.7, 123.0, 117.8, 117.3, 67.3, 64.5, 64.0 and 20.5.

Example 17

Synthesis of α-(3-Ethoxy-4-methoxyphenyl)-N-isopropyinitrone

The title compound was prepared according to the procedures described in Examples 11 using 3-ethoxy-4-methoxybenzaldehyde and N-isopropylhydroxylamine. The title compound was isolated in 43.9% yield as a solid, m.p. 80.8° C. (R$_f$=0.15 on a silica gel plate using ethyl acetate as the eluant).

Spectroscopic data were as follows:

IR (KBr, cm$^{-1}$): 2981.6 (CH), 1596.7 (C=N), 1443.7 (CH$_3$), 1263.3 (C—O—C) and 1128.6 (N—O).

$^1$H NMR (CDCl$_3$, 270 MHz): δ=8.44 (1H, d, J=1.9 Hz, phenyl H), 7.40 (1H, dd, J=8.5 & 1.9 Hz, phenyl H), 7.34 (1H, s, nitronyl CH), 6.87 (1H, d, J=8.5 Hz, phenyl H), 4.16 (3H, m, CH$_2$ and CH), 3.89 (3H, s, CH$_3$) and 1.48 (9H, m, 3 CH$_3$).

$^{13}$C NMR (CDCl$_3$, 67.9 MHz): δ=151.0, 148.2, 132.2, 124.2, 123.0, 112.3, 110.9, 67.2, 64.1, 55.7, 20.5 and 14.4.

Example 18

Synthesis of α-(2-Ethoxyphenyl)-N-isopropylnitrone

The title compound was prepared according to the procedure described in Example 11 using 2-ethoxybenzaldehyde and N-isopropylhydroxylamine. The title compound was isolated in 48.8% yield as a solid, m.p. 59.4° C. (R$_f$=0.48 on a silica gel plate using ethyl acetate as the eluant).

Spectroscopic data were as follows:

IR (KBr, cm$^{-1}$): 2978.8 (CH), 1593.6 (C=N), 1245.0 (C—O—) and 1149.3 (N—O).

$^1$H NMR (CDCl$_3$, 270 MHz): δ=9.30 (1H, d, J=7.7 Hz, phenyl H), 7.961 (1H, s, nitronyl H), 7.30 (1H, td, J=7.7 & 1.7 Hz, phenyl H), 6.98 (1H, td, J=7.7 & 1.7 Hz, phenyl H), 6.83 (1H, d, J=7.7 Hz, phenyl H), 4.23 (1H, m, CH), 4.03 (2H, quartet, J=7.2 Hz, CH$_2$) and 1.44 (9H, m, 3 CH$_3$).

$^{13}$C NMR (CDCl$_3$, 67.9 MHz): δ=156.56, 131.38, 129.02, 126.76, 120.80, 120.04, 110.75, 67.95, 63.78, 20.55 and 14.39.

Example 19

Synthesis of α-(2-Ethoxyphenyl)-N-cyclohexylnitrone

The title compound was prepared according to the procedure described in Example 11 using 2-ethoxybenzaldehyde and N-cyclohexylhydroxylamine. The title compound was isolated in 89% yield as a solid. m.p. 54.8° C.

Spectroscopic data were as follows:

IR (KBr, cm$^{-1}$): 2932.9 (CH), 1593.8 (C=N), 1244.9 (C—O—) and 1144.8 (N—O).

$^1$H NMR (CDCl$_3$, 270 MHz): δ=9.32 (1H, d, J=7.9 Hz, phenyl H), 7.89 (1H, s, nitronyl H), 7.29 (1H, t, J=7.9 Hz, phenyl H), 6.97 (1H, t, J=7.9 Hz, phenyl H), 6.84 (1H, d, J=7.9 Hz, phenyl H), 4.06 (2H, quartet, J=7.1 Hz, CH$_2$), 3.84 (1H, m, CH), 1.95 (6H, m, 2 CH$_2$ & 2 CH), 1.67 (1H, m, CH), 1.66 (3H, t, J=7.1 Hz, CH$_3$) and 1.25 (3H, m, 3 CH).

$^{13}$C NMR (CDCl$_3$, 67.9 MHz): δ=156.6, 131.3, 129.0, 127.1, 120.8, 120.1, 110.7, 75.8, 63.8, 30.8, 24.7 and 14.4.

Example 20

Synthesis of α-(4-Benzyloxy-3-methoxyphenyl)-N-isopropylnitrone

The title compound was prepared according to the procedures described in Examples 11 using 4-benzyloxy-3-methoxybenzaldehyde and N-isopropylhydroxylamine. The title compound was isolated in 54.6% yield as a solid, m.p. 95.5° C.

Spectroscopic data were as follows:

IR (KBr, cm$^{-1}$): 2988.4 (CH), 2935.0 (CH), 1585.1 (C=N), 1461.0 (CH$_3$), 1262.9 (C—O—) and 1126.9 (N—O).

$^1$H NMR (CDCl$_3$, 270 MHz): δ=8.50 (1H, d, J=1.7 Hz, phenyl H), 7.33 (7H, m, 6 phenyl H & nitronyl H), 6.86 (1H, d, J=8.4 Hz, phenyl H), 5.18 (2H, s, CH$_2$), 4.13 (1H, septet, J=6.4 Hz, CH), 3.93 (3H, s, CH$_3$) and 1.47 (6H, d, J=6.4 Hz, 2 CH$_3$).

$^{13}$C NMR (CDCl$_3$, 67.9 MHz): δ=149.8. 149.4, 136.9, 132.2. 128.8, 128.2, 127.4, 124.6, 122.9, 113.2, 111.5, 70.7, 67.3, 55.7 and 20.5.

Example 21

Using the procedures described herein, the following compound was prepared:

α-(4-Ethoxy-3-methoxyphenyl)-N-isopropylnitrone.

Example 22

Synthesis of α-(3-Ethoxy-4-hexyloxyphenyl)-N-cyclohexylnitrone

The title compound was prepared according to the procedure described in Example 28 using 3-ethoxy-4-hydroxybenzaldehyde, 1-iodohexane and N-cyclohexylhydroxylamine. The title compound was isolated in 41.3% yield as a solid, m.p. 67.3° C.

Spectroscopic data were as follows:

IR (KBr, cm$^{-1}$): 2920.7 (CH), 1597.7 (C=N), 1341.2 (CH$_3$), 1267.7 (C—O—C), and 1129.0 (N—O).

$^1$H NMR (CDCl$_3$, 270 MHz): δ=8.36 (1H, d, J=1.9 Hz, phenyl H), 7.39 (1H, dd, J=8.6 & 1.9 Hz, phenyl H), 7.31 (1H, s, nitronyl H), 6.84 (1H, d, J=8.6 Hz, phenyl H), 4.12 (2H, quartet, J=7.0 Hz, CH$_2$), 4.01 (2H, t, J=6.8 Hz, CH$_2$), 3.76 (1H, m, CH), 1.93 (10H, m, 5 CH$_2$), 1.42 (3H, t, J=7.0 Hz, CH$_3$), 1.32 (8H, m, 4 CH$_2$) and 0.88 (3H, t, J=7.0 Hz, CH$_3$).

$^{13}$C NMR (CDCl$_3$, 67.9 MHz): δ=150.8, 157.6, 132.6, 124.2, 123.0, 113.2, 112.6, 75.1, 69.0, 64.4, 31.3, 30.8, 28.7, 25.3, 24.8, 22.2, 14.4 and 13.6.

Example 23

Synthesis of α-(4-Benzyloxy-3-methoxyphenyl)-N-n-butylnitrone

The title compound was prepared according to the procedures described in Examples 11 using 4-benzyloxy-3-methoxybenzaldehyde and N-n-butylhydroxylamine. The title compound was isolated in 41.7% yield as a solid, m.p. 81.2° C.

Spectroscopic data were as follows:

IR (KBr, cm$^{-1}$): 2925.1 (CH), 2856.9 (CH), 1593.2 (C=N), 1463.1 (CH$_3$), 1263.1 (C—O—) and 1156.1 (N—O).

$^1$H NMR (CDCl$_3$, 270 MHz): δ=8.42 (1H, d, J=2.0 Hz, phenyl H), 7.34 (7H, m, 6 phenyl H & nitronyl H), 6.86 (1H, d, J=8.4 Hz, phenyl H), 5.18 (2H, s, CH$_2$), 3.93 (3H, s, CH$_3$), 3.93 (2H, t, J=7.3 Hz, CH$_2$), 1.96 (2H, quintet, J=7.3 Hz, CH$_2$), 1.39 (2H, sextet, J=7.3 Hz, CH$_2$) and 0.95 (3H, t, J=7.3 Hz, CH$_3$).

$^{13}$C NMR (CDCl$_3$, 67.9 MHz): δ=150.0, 149.4, 136.9, 134.3, 128.8, 128.2, 127.4, 124.4, 122.9, 113.2, 111.4, 70.7, 66.6, 55.8, 29.4, 19.4 and 13.2.

Example 24

Using the procedures described herein, the following compound was prepared:

α-(4-Ethoxy-3-methoxyphenyl)-N-n-butylnitrone.

Example 25

Synthesis of α-(2-Ethoxyphenyl)-N-n-butylnitrone

The title compound was prepared according to the procedures described in Examples 11 using 2-ethoxybenzaldehyde and N-n-butylhydroxylamine. The title compound was isolated in 44.5% yield as a liquid.

Spectroscopic data were as follows:

IR (NaCl, cm$^{-1}$): 2959.6 (CH), 1594.9 (C=N), 1454.8 (CH$_3$), 1245.1 (C—O—C) and 1163.5 (N—O).

$^1$H NMR (CDCl$_3$, 270 MHz): δ=9.24 (1H, d, J=8.0 Hz, phenyl H), 7.80 (1H, s, nitronyl H), 7.28 (1H, t, J=8.0 Hz, phenyl H), 6.95 (1H, t, J=8.0 Hz, phenyl H), 6.81 (1H, d, J=8.0 Hz, phenyl H). 4.02 (2H, quartet, J=6.35 Hz, CH$_2$), 3.90 (2H, t, J=7.1 Hz, CH$_2$), 1.93 (2H, quintet, J=7.3 Hz, CH$_2$), 1.40 (5H, m, CH$_2$ & CH$_3$) and 0.93 (3H, t, J=7.4 Hz, CH$_3$).

$^{13}$C NMR (CDCl$_3$, 67.9 MHz): δ=156.6. 131.5, 129.0, 128.9, 120.7, 119.9, 110.8, 67.2, 63.8, 29.5, 19.3, 14.3 and 13.2.

Example 26

Synthesis of α-(3-Ethoxy-4-methoxyphenyl)-N-n-butylnitrone

The title compound was prepared according to the procedures described in Examples 11 using 3-ethoxy-4- methoxybenzaldehyde and N-n-butylhydroxylamine. The title compound was isolated in 41.1% yield as a solid, m.p. 117.3° C.

Spectroscopic data were as follows:

IR (KBr, cm$^{-1}$): 2953.1 (CH), 1593.9 (C=N), 1265.4 (C—O—C) and 1129.3 (N—O).

$^1$H NMR (CDCl$_3$, 270 MHz): δ=8.35 (1H, d, J=1.8 Hz, phenyl H), 7.42 (1H, dd, J=8.5 & 1.8 Hz, phenyl H), 7.27 (1H, s, nitronyl H), 6.86 (1H, d, J=8.5 Hz, phenyl H), 4.16 (2H, quartet, J=6.9 Hz, CH$_2$), 3.87 (5H, m, CH$_2$ and CH$_3$), 1.94 (2H, quintet, J=7.4 Hz, CH$_2$), 1.45 (5H, m, CH$_2$ and CH$_3$) and 0.95 (3H, t, J=7.4 Hz, CH$_3$).

$^{13}$C NMR (CDCl$_3$, 67.9 MHz): δ=151.2, 148.2, 132.3, 124.1, 122.9, 112.3, 111.0, 66.6, 64.2, 55.7, 29.4, 19.4, 14.3 and 13.2.

Example 27

Synthesis of α-(3-Ethoxy-4-hexyloxyphenyl)-N-isopropylnitrone

The title compound was prepared according to the procedure described in Example 28 using 3-ethoxy-4-hydroxybenzaldehyde, 1-iodohexane and N-isopropylhydroxylamine. The title compound was isolated in 47.1% overall yield as a solid, m.p. 69.0° C.

Spectroscopic data were as follows:

IR (KBr, cm$^{-1}$): 2995.0 (CH), 1596.9 (C=N), 1393.8 (iPr), 1261.2 (C—O—C) and 1128.7 (N—O).

$^1$H NMR (CDCl$_3$, 270 MHz): δ=8.36 (1H, d, J=2.0 Hz, phenyl H), 7.40 (1H, dd, J=8.4 & 2.0 Hz, phenyl H), 7.32 (1H, s, nitronyl H), 6.86 (1H, d, J=8.4 Hz, phenyl H), 4.13 (3H, m, CH$_2$ and CH), 4.02 (2H, t, J=6.9 Hz, CH$_2$), 1.82 (2H, quintet, J=7.4 Hz, CH$_2$), 1.48 (6H, d, J=6.7 Hz, 2 CH$_3$), 1.42 (3H, t, J=6.9 Hz, CH$_3$), 1.31 (6H, m, 3 CH$_2$) and 0.88 (3H, t, J=6.9 Hz, CH$_3$).

$^{13}$C NMR (CDCl$_3$, 67.9 MHz): δ=150.8, 148.6, 132.2, 124.1, 123.1, 133.2, 112.6, 69.0, 67.2, 64.4, 31.3, 28.7, 25.3, 22.2, 20.5, 14.4 and 13.6.

Example 28

Synthesis of α-(3-Ethoxy-4-hexyloxyphenyl)-N-tert-butyinitrone

A solution of 3-ethoxy4-hydroxybenzaldehyde (13.28 g, 79.9 mmol) and sodium hydroxide (3.20 g, 79.9 mmol) in ethanol (120 mL) was refluxed for 30 min. To the refluxing solution was added 1-iodohexane (18.6 g, 87.9 mmol) in one portion and reflux was continued for 24 h. The solution was then cooled and the ethanol removed on a rotary evaporator. The residue was dissolved in ethyl acetate and this solution filtered and rotary evaporated. The resulting residue was reacted with N-tert-butylhydroxylamine (6.94 g) in 200 mL of benzene in the presence of p-toluenesulfonic acid (0.8 g) at refluxing temperature for 24 h. After evaporation, the residue obtained was purified by recrystallization from hexanes to give the title compound (11.02 g, 57.2% overall yield) as a solid, m.p. 35.5° C.

Spectroscopic data were as follows:

IR (KBr, cm$^{-1}$): 2900 (CH), 1596.2 (C=N), 1361.1 (CH$_3$), 1276.0 (C—O—C) and 1144.8 (N—O).

$^1$H NMR (CDCl$_3$, 270 MHz): δ=8.38 (1H, d, J=1.7 Hz, phenyl H), 7.45 (1H, dd, J=8.5 & 1.7 Hz, phenyl H), 7.42 (1H, s, nitronyl H), 6.86 (1H, d, J=8.5 Hz, phenyl H), 4.13 (2H, quartet, J=7.0 Hz, CH$_2$), 4.02 (2H, t, J=6.8 Hz, CH$_2$), 1.82 (2H, m, CH$_2$), 1.65 (2H, m, CH$_2$), 1.58 (9H, s, 3 CH$_3$), 1.42 (3H, t, J=7.0 Hz, CH$_3$), 1.31 (4H, m, 2 CH$_2$) and 0.88 (3H, t, J=6.3 Hz, CH$_3$).

$^{13}$C NMR (CDCl$_3$, 67.9 MHz): δ=150.8, 148.6, 130.1, 124.4, 123.4, 113.4, 112.6, 70.0, 69.0, 64.4, 31.3, 28.7, 28.0, 25.3, 22.2, 14.4 and 13.6.

Example 29

Synthesis of α-(2-Fluoro-4-octyloxyphenyl)-N-tert-butylnitrone

To dry dimethylformamide (200 mL) were added 2-fluoro-4-hydroxybenzonitrile (13.71 g, 100 mmol), 1-iodooctane (28.82 g, 120 mmol) and potassium fluoride (11.6 g, 200 mmol). This mixture was stirred at room temperature for 16 h, and then at 50° C. for 2 h and then at 90° C. for 2 h. The mixture was then poured into wet-ice (400 g) and 37% HCl (10 mL). The resulting solution was extracted with diethyl ether (3×200 mL). The ether layer was washed with water (2×200 mL) and dried over Na$_2$SO$_4$. After filtration, rotary evaporation gave the crude desired intermediate 2-fluoro-4-n-octyloxybenzonitrile (27.83 g). This liquid intermediate was then added, over a 5–10 min period at 3–13° C. to a flask containing LiAlH(OEt)$_3$ [which had been freshly prepared from LiAlH$_4$ (5.03 g, 0.1326 mol) and ethyl acetate (15.24 g, 0.1730 mol) at 3–8° C. in diethyl ether (130 mL)]. The reaction mixture was stirred at 5° C. for 75 min and 5 N H$_2$SO$_4$ aqueous solution (120 mL) was added dropwise with cooling. After separation, the aqueous layer was extracted with diethyl ether (2×100 mL) and the combination extracts were washed with water (2×100 mL). Standard work-up procedures afforded crude 2-fluoro-4-n-octyloxybenzaldehyde (26.07 g). The crude material was then mixed with N-tert-butylhydroxylamine (8.6 g, 96.4 mmol), molecular sieves (50 g, 4 A) and silica gel (10 g) in chloroform (250 mL). The mixture was stirred at room temperature for 23 h and refluxed for 3 h under argon gas. The mixture was then filtered and rotary evaporated to give a residue which was purified by column chromatography over silica gel eluted with hexanes/ethyl acetate (4:1, v:v). The title compound (12.90 g) was obtained in 39.9% overall yield as a slightly yellowish solid. m.p. 35.6° C. ($R_f$=0.36 on a silica gel plate using hexanes/EtOAc, 4:1, v:v, as the eluant).

Spectroscopic data were as follows:

IR (KBr, cm$^{-1}$): 2928.1 (CH), 2855.1 (CH), 1617.8 (C=N), 1556.8 (benzene ring), 1287.0 (Ar—F), 1161.2 (Ar—O), 1129.4 (N—O) and 1105.4 (alkyl-O).

$^1$H NMR (CDCl$_3$, 270 MHz): δ=9.288 (1H, t, $J_H$=$J_F$=8.9 Hz, aromatic H), 7.702 (1H, s, CH=N), 6.684 (1H, dd, $J_H$=8.9 Hz, $J_H$=2.5 Hz, aromatic H), 6.586 (1H, dd, $J_F$=13.7 Hz, $J_H$=2.5 Hz, aromatic H), 3.937 (2H, t, J=6.6 Hz, OCH$_2$), 1.745 (2H, m, CH$_2$), 1.568 (9H, s, 3 CH$_3$), 1.408–1.251 (10H, m, (CH$_2$)$_5$) and 0.851 (3H, t, J=6.9 Hz, CH$_3$).

$^{13}$C NMR (CDCl$_3$, 67.9 MHz): δ=161.959 (d, J=11.4 Hz), 161.959 (d, J=253.9 Hz), 130.103, 122.232 (d, J=8.3 Hz), 112.363 (d, J=8.3 Hz), 109.892, 101.693 (d, J=25.9 Hz), 70.630, 68.372, 31.459, 28.958, 28.851, 28.683, 27.936, 25.587, 22.261 and 13.658.

Example 30

Synthesis of α-(2,4,6-Triethoxyphenyl)-N-tert-butylnitrone

The title compound was prepared according to the procedure described in Example 11 using 2,4,6- triethoxybenzaldehyde and N-tert-butylhydroxylamine. The title compound was isolated in 92.3% yield as a solid, m.p. 109.1° C.

Spectroscopic data were as follows:

IR (KBr, cm$^{-1}$): 2978.5 (CH), 1608.2 (C=N), 1438.6 (CH$_3$), 1231.2 (C—O—C) and 1132.3 (N—O).

$^1$H NMR (CDCl$_3$, 270 MHz): δ=7.46 (1H, s, nitronyl H), 6.07 (2H, s, 2 phenyl H), 3.98 (6H, m, 3 CH$_2$), 1.56 (9H, s, 3 CH$_3$) and 1.32 (9H, m, 3 CH$_3$).

$^{13}$C NMR (CDCl$_3$, 67.9 MHz): δ=161.9, 159.3, 125.0, 92.3, 69.3, 63.9, 63.4, 28.1, 14.5 and 14.3.

Example 31

Synthesis of α-(2,4,6-Triethoxyphenyl)-N-cyclohexylnitrone

The title compound was prepared according to the procedure described in Example 11 using 2,4,6-triethoxybenzaldehyde and N-cyclohexylhydroxylamine. The title compound was isolated in 87.4% yield as a solid, m.p. 145.7° C.

Spectroscopic data were as follows:

IR (KBr, cm$^{-1}$): 2935 (CH), 1601 (C=N), 1391 (CH$_3$), 1167 (C—O—C) and 1133 (N—O).

$^1$H NMR (CDCl$_3$, 270 MHz): δ=7.34 (1H, s, nitronyl H), 6.06 (2H, s, 2 phenyl H), 3.99 (6H, m, 3 CH$_2$), 3.80 (1H, m, CH), 1.94 (10H, m, 5 CH$_2$) and 1.32 (9H, m, 3 CH$_3$).

$^{13}$C NMR (CDCl$_3$, 67.9 MHz): δ=162.1, 159.4, 127.2, 102.0, 92.2, 74.1, 64.0, 63.4, 31.0, 29.6, 24.8, 14.5 and 14.4.

Example 32

Synthesis of α-(2-n-Butoxyphenyl)-N-tert-butylnitrone

The title compound was prepared according to the procedure described in Example 28 using 2-hydroxybenzonitrile, 1-iodobutane and N-tert-butylhydroxylamine. The title compound was isolated in 77.4% overall yield as a viscous oil.

Spectroscopic data were as follows:

IR (NaCl, cm$^{-1}$): 3074 (Ar CH), 2962 (CH), 1594 (C=N), 1468 (CH$_3$), 1244 (C—O—) and 1132 (N—O).

$^1$H NMR (CDCl$_3$, 270 MHz): δ=9.29 (1H, dd, J=7.9 & 1.7 Hz, phenyl H), 8.06 (1H, s, nitronyl H), 7.29 (1H, td, J=7.9 & 1.7 Hz, phenyl H), 6.96 (1H, t, J=7.9 Hz, phenyl H), 6.82 (1H, d, J=7.9 Hz, phenyl H), 3.98 (2H, t, J=6.3 Hz, CH$_2$), 1.75 (2H, quintet, J=6.9 Hz, CH$_2$), 1.57 (9H, m, 3 CH$_3$), 1.50 (2H, m, CH$_2$) and 0.96 (3H, t, J=7.3 Hz, CH$_3$).

$^{13}$C NMR (CDCl$_3$, 67.9 MHz): δ=157.1, 131.4, 128.8, 124.7, 120.7, 120.4, 110.8, 70.7, 67.9, 30.9, 28.0, 19.0 and 13.4.

Example 33

Synthesis of α-(3,4-Diethoxyphenyl)-N-tert-butyinitrone

The title compound was prepared according to the procedure described in Example 11 using 3,4-diethoxybenzaldehyde and N-tert-butylhydroxylamine. The title compound was isolated in 93.7% yield as a solid. m.p. 57.9° C.

Spectroscopic data were as follows:

IR (KBr, cm$^{-1}$): 2984 (CH), 1596 (C=N), 1272 (C—O—) and 1146 (N—O).

$^1$H NMR (CDCl$_3$, 270 MHz): δ=8.41 (1H, d, J=1.9 Hz, phenyl H), 7.46 (1H, dd, J=8.4 & 1.9 Hz, phenyl H), 7.43 (1H, s, nitronyl H), 6.86 (1H, d, J=8.4 Hz, phenyl H), 4.14 (2H, quartet, J=7.0 Hz, CH$_2$), 4.13 (2H, quartet, J=7.0 Hz, CH$_2$), 1.58 (9H, s, 3 CH$_3$), 1.45 (3H, t, J=7.0 Hz, CH$_3$) and 1.44 (3H, t, J=7.0 Hz, CH$_3$).

$^{13}$C NMR (CDCl$_3$, 67.9 MHz): δ=150.5, 148.4, 130.2, 124.4, 123.4, 113.0, 112.3, 70.1, 64.3, 28.0, 14.4 and 14.3.

Example 34

Synthesis of α-(2-Fluoro-4-heptyloxyphenyl)-N-tert-butylnitrone

The title compound was prepared according to the procedure described in Example 28 using 2-fluoro-4-hydroxybenzonitrile. 1-iodoheptane and N-tert-butylhydroxylamine. The title compound was isolated in 66.0% overall yield as a white solid, m.p. 38.8° C. (R$_f$=0.21 on a silica gel plate using hexanes/ethyl acetate, 4:1, v:v, as the eluant).

Spectroscopic data were as follows:

IR (KBr, cm$^{-1}$): 2930.1 (CH), 2857.5 (CH), 1618.6 (C=N), 1556.6 (benzene ring), 1286.8 (Ar—F), 1161.6 (Ar—O), 1129.4 (N—O) and 1105.4 (alkyl-O).

$^1$H NMR (CDCl$_3$, 270 MHz): δ=9.291 (1H, t, J$_H$=J$_F$=8.9 Hz, aromatic H), 7.723 (1H, s, CH=N), 6.700 (1H, dd, J$_H$=8.9 Hz, J$_H$=2.6 Hz, aromatic H), 6.603 (1H, dd, J$_F$=13.1 Hz, J$_H$=2.6 Hz, aromatic H), 3.954 (2H, t, J=6.6 Hz, OCH$_2$), 1.747 (2H, m, CH$_2$), 1.585 (9H, s, 3 CH$_3$), 1.445–1.286 (8 H, m, (CH$_2$)$_4$) and 0.872 (3H, t, J=6.8 Hz, CH$_3$).

$^{13}$C NMR (CDCl$_3$, 67.9 MHz): δ=161.997 (d, J=12.4 Hz), 161.990 (d, J=253.9 Hz), 130.133, 122.354 (d, J=8.3 Hz), 112.332 (d, J=8.3 Hz), 109.922, 101.716 (d, J=24.9 Hz), 70.645, 68.387, 31.429, 28.683, 27.951, 25.556, 22.216 and 13.658.

Example 35

Synthesis of α-(2-Fluoro-4-ethoxyphenyl)-N-tert-butylnitrone

The title compound was prepared according to the procedure described in Example 29 using 2-fluoro-4-hydroxybenzonitrile, ethyl iodide and N-tert-butylhydroxylamine. The title compound was isolated in 64.7% overall yield as slightly yellowish crystals. m.p. 82.5° C. (R$_f$=0.16 on a silica gel plate using hexanes/ethyl acetate, 4:1, v:v, as the eluant).

Spectroscopic data were as follows:

IR (KBr, cm$^{-1}$): 2978.4 (CH), 2938.0 (CH), 1616.3 (C=N), 1560.7 (benzene ring), 1290.0 (Ar—O), 1128.7 (N—O), 1112.9 (Ar—F) and 1042.3 (alkyl-O).

$^1$H NMR (CDCl$_3$, 270 MHz): δ=9.300 (1H, t, J=9.0 Hz, aromatic H), 7.716 (1H, s, nitronyl CH), 6.695 (1H, dd, J=9.0 Hz, J=2.4 Hz, aromatic H), 6.597 (1H, dd, J=13.1 Hz, J=2.4 Hz, aromatic H), 4.035 (2H, q, J=6.9 Hz, OCH$_2$), 1.581 (9H, s, 3 CH$_3$) and 1.396 (3H, t, J=6.9 Hz, CH$_3$).

$^{13}$C NMR (CDCl$_3$, 67.9 MHz): δ=161.952 (d, J$_F$=254.9 Hz), 161.738 (d, J$_F$=12.4 Hz), 130.118, 122.285 (d, J$_F$=9.3 Hz), 112.409 (d, J$_F$=8.3 Hz), 109.846, 101.708 (d, J$_F$=25.9 Hz), 70.660, 63.842, 27.936 and 14.177.

Example 36

Synthesis of α-(2-Fluoro-4-ethoxyphenyl)-N-cyclohexylnitrone

The title compound was prepared according to the procedure described in Example 29 using 2-fluoro-4- hydroxybenzonitrile, ethyl iodide and N-cyclohexylhydroxylamine. The title compound was isolated in 58.8% overall yield as slightly yellowish crystals, m.p. 112.7° C. ($R_f$=0.17 on a silica gel plate using hexanes/ethyl acetate, 4:1, v:v, as the eluant).

Spectroscopic data were as follows:

IR (KBr, cm$^{-1}$): 2956.5 (CH), 2933.2 (CH), 1616.9 (C=N), 1558.7 (benzene ring), 1287.4 (Ar—O), 1158.7 (N—O), 1103.5 (Ar—F) and 1039.6 (alkyl-O).

$^1$H NMR (CDCl$_3$, 270 MHz): δ=9.245 (1H, t, J=9.0 Hz, aromatic H), 7.580 (1H, s, nitronyl CH), 6.689 (1H, dd, J=9.0 Hz, J=2.5 Hz, aromatic H), 6.580 (1H, dd, J=14.3 Hz, J=2.5 Hz, aromatic H), 4.022 (2H, q, J=6.9 Hz, OCH$_2$), 3.805 (1H, tt, J=11.3 Hz, J=4.1 Hz, N—CH), 2.069–1.990 (2H, m, cyclohexyl 2H), 1.958–1.862 (4H, m, cyclohexyl 4H), 1.694–1.651 (1H, m, cyclohexyl H), 1.386 (3H, t, J=6.9 Hz, CH$_3$) and 1.333–1.176 (3H, m, cyclohexyl 3H).

$^{13}$C NMR (CDCl$_3$, 67.9 MHz): δ=161.734 (d, $J_F$=13.0 Hz), 161.639 (d, $J_F$=253.9 Hz), 130.255, 124.703 (d, $J_F$=8.3 Hz), 112.165 (d, $J_F$=8.3 Hz), 109.953, 101.731 (d, $J_F$=24.9 Hz), 75.587, 63.857, 30.819, 24.702 and 14.177.

Examples 37–38

Using the procedures described herein, the following compounds were prepared:

α-(2-Ethoxyphenyl)-N-1-adamantylnitrone, and
α-(3-Ethoxy-4-methoxyphenyl)-N-1-adamantylnitrone.

Example 39

Synthesis of α-(4-Ethoxyphenyl)-N-cyclopentylnitrone

4-Ethoxybenzaldehyde (22.0 g, 0.1467 mol) and N-cyclopentylhydroxylamine (14.1 g, 0.1398 mol) were mixed into toluene (200 mL) with p-toluenesulfonic acid monohydrate (1.0 g, 5.26 mmol). The mixture was refluxed for 3 hrs under argon atmosphere with a Dean-Stark trap to remove generated water. The solution was rotary evaporated to give a residue which was purified by flash chromatography over silica gel with EtOAc as an eluant and then recrystallization from a mixed solvent of hexanes and EtOAc. The title compound was obtained as a solid (21.24 g 65.1% yield), m.p. 95.1° C. ($R_f$=0.18 on a silica gel plate using hexanes:EtOAc, 2:1, v/v, as an eluant).

Spectroscopic data were as follows:

IR (KBr, cm$^{-1}$): 2977 (CH), 2873 (CH), 1601 (C=N & benzene ring), 1575 (benzene ring), 1251 (Ar—O) and 1169 (N—O).

$^1$H NMR (CDCl$_3$, 270 MHZ): δ=8.22 (2H, d, J=9.0 Hz, aromatic 2H), 7.41 (1H, s, CH=N), 6.91 (2H,d, J=9.0 Hz, aromatic 2H), 4.40 (1H, tt, J=6.3 & 7.8 Hz, CH), 4.07 (2H, q, J=7.0 Hz, OCH$_2$), 2.33–2.20 (2H, m, cyclopentyl 2H), 2.04–1.86 (4H, m, cyclopentyl 4H), 1.70–154 (2H, m, cyclopentyl 2H), and 1.42 (3H, t, J=7.0 Hz, CH$_3$) ppm.

$^{13}$C NMR (CDCl$_3$, 67.9 MHZ): δ=160.13, 132.45, 130.39, 125.56, 114.19, 75.72, 63.45, 31.25, 25.56 and 14.66 ppm.

Example 40

Synthesis of α-(4-Ethoxyphenyl)-N-tert-octylnitrone

The title compound was prepared by oxidation of N-(4-ethoxyphenyl)-N-tert-octylamine with m-chloroperoxybenzoic acid in methylene chloride. The amine was synthesized via NaBH$_4$ reduction from the corresponding imine which was acquired by condensation of 4-ethoxybenzaldehyde and tert-octylamine in methanol. The title compound was isolated in 65.0% overall yield as white crystals, m.p. 100.8° C. ($R_f$=0.33 on silica gel plate using hexanes:EtOAc, 7:3, v/v, as an eluant).

Spectroscopic data were as follows:

IR (Kbr, cm$^{-1}$): 2978 & 2951 (CH), 1605 (C=N & benzene ring), 1563 (benzene ring), 1263 (Ar—O) and 1114 (N—O).

$^1$H NMR (CDCl$_3$, 270 MHZ): δ=8.27 (2H, d, J=9.0 Hz, aromatic 2H), 7.49 (1H, s, CH=N), 6.91 (2H,d, J=9.0 Hz, aromatic 2H), 4.08 (2H, q, J=7.0 Hz, OCH$_3$), 1.97 (2H, s, CH$_2$), 1.64 (6H, s, 2 CH$_3$), 1.42 (3H, t, J=7.0 Hz, CH$_3$) and 0.97, (9H, s, 3 CH$_3$) ppm.

$^{13}$C NMR (CDCl$_3$, 67.9 MHZ): δ=160.12, 130.55, 130.17, 124.11, 114.20, 73.20, 63.49, 51.35, 31.61, 30.69, 28.82 and 14.72 ppm.

Example 41

Synthesis of α-(4-Benzyloxyphenyl)-N-tert-butylnitrone

A mixture of 4-benzyloxybenzaldehyde, N-tert-butylhydroxylamine and catalytic amount of p-toluenesulfonic acid monohydrate in benzene was refluxed under argon atmosphere with a Dean-Stark trap to remove generated water. The mixture was then rotary evaporated to give a residue which was purified by recrystallization. The title compound was obtained in 89.3% yield as a white powder, m.p. 111.0° C. ($R_f$=0.66 on a silica gel plate using EtOAc as an eluant).

Spectroscopic data were as follows:

IR (KBr, cm$^{-1}$): 2982 (CH), 1601 (C=N & benzene ring), 1508 (benzene ring), 1242 (Ar—O), 1170 (N—O), and 1005 (benzyl-O)

$^1$H NMR (CDCl$_3$, 270 MHZ): δ=8.29 (2H, d, J=9.2 Hz, aromatic 2H), 7.46 (1H, s, CH=N), 7.41–7.31 (5H, m, aromatic 5H), 7.00 (2H, d, J=9.2 Hz, aromatic 2H), 5.10 (2H, s, OCH$_2$), and 1.60 (9H, s, 3 CH$_3$) ppm.

$^{13}$C NMR (CDCl$_3$, 67.9 MHZ): δ=159.89, 136.47, 130.64, 129.35, 128.52, 128.00, 127.42, 124.23, 114.58, 70.05, 69.91 and 28.25 ppm Example 42

Synthesis of α-(4-Benzyloxyphenyl)-N-cyclopentylnitrone

A mixture of 4-benzyloxybenzaldehyde (20 g, 94.23 mmol), N-cyclopentylhydroxylamine (14.3 g, 141.34 mmol), molecular sieves (60 g, 4A) and silica gel (15 g) in chloroform (300 mL) was stirred at room temperature under argon atmosphere for 48 hrs and then was refluxed for an additional 3 hrs. The mixture was filtered and rotary evaporated to give crystals which were recrystallized from hexanes and EtOAc to provide the title compound as white crystals, 23.7 g, 85.1% yield), m.p. 115.1° C. ($R_f$=0.35 on a silica gel plate using hexanes:EtOAc, 1:1, v:v, as an eluant).

Spectroscopic data were as follows:

IR (KBr, cm$^{-1}$): 2953 (CH), 2867 (CH), 1601 (C=N & benzene ring), 1505 (benzene ring), 1251 (Ar . O), 1139 (N—O), and 1009 (benzyl-O).

$^1$H NMR (CDCl$_3$, 270 MHZ): δ=8.23 (2H, d, J=9.2 Hz, aromatic 2H), 7.40 (1H, s, CH=N), 7.43–7.27 (5H, m, aromatic 5H), 6.98 (2H, d, J=9.2 Hz, aromatic 2H), 5.08 (2H, s, OCH$_2$), 4.36 (1H, tt, J=7.7 & 6.1 Hz, CH), 2.33–2.20 (2H, m, cyclopentyl 2H), 2.04–1.86 (4H, m, cyclopentyl 4H), 1.70–1.54 (2H, m, cyclopentyl 2H) ppm.

$^{13}$C NMR (CDCl$_3$, 67.9 MHZ): δ=159.79, 136.39, 132.21, 130.30, 128.47, 127.94, 127.36, 123.96, 114.56, 75.71, 69.85, 31.21 and 25.50 ppm Example 43

Synthesis of α-(4-Benzyloxyphenyl)-N-cyclohexylnitrone

The title compound was prepared according to the procedure described in Example 42 using 4-benzyloxybenzaldehyde and N-cyclohexylhydroxylamine. The title compound was obtained in 81.2% yield as slightly yellowish solid, m.p. 129.0° C. (R$_f$=0.30 on a silica gel plate using hexanes:EtOAc, 1:1, v:v, as an eluant).

Spectroscopic data were as follows:

IR (KBr, cm$^{-1}$): 2993 (CH), 2854 (CH), 1603 (C=N & benzene ring), 1507 (benzene ring), 1251 (Ar—O), 1138 (N—O), and 1012 (benzyl-O)

$^1$H NMR (CDCl$_3$, 270 MHZ): δ=8.24 (2H, d, J=8.9 Hz, aromatic 2H), 7.35 (1H, s, CH=N), 7.44–7.32 (5H, m, aromatic 5H), 7.00 (2H, d, J=8.9 Hz, aromatic 2H), 5.11 (2H, s, OCH$_2$), 3.79 (1H, m, CH), 2.10–1.89 (6H, m, cyclopentyl 6H), 1.70 (1H, m, cyclopentyl 1H), and 1.22–1.45 (3H, m, cyclopentyl 3H) ppm.

$^{13}$C NMR (CDCl$_3$, 67.9 MHZ): δ=159.90, 136.51, 131.70, 130.44, 128.58, 128.05, 127.45, 124.05, 114.68, 75.14, 69.97, 31.12 and 25.09 ppm.

Example 44

Synthesis of α-(2-Ethoxyphenyl)-N-cyclopentylnitrone

The title compound was prepared according to the procedure described in Example 42 using 2-ethoxybenzaldehyde and N-cyclopentylhydroxylamine. The title compound was obtained in 72.6% yield as white crystals, m.p. 87.3° C. (R$_f$=0.43 on a silica gel plate using hexanes:EtOAc, 2:1, v:v, as an eluant).

Spectroscopic data were as follows:

IR (KBr, cm$^{-1}$): 2976 (CH), 2957 (CH), 1636 (C=N), 1597 & 1564 (benzene ring), 1251 (Ar—O), 1165 (N—O), and 1043 (Et—O).

$^1$H NMR (CDCl$_3$, 270 MHZ): δ=9.33 (1H, dd, J=7.8 & 1.7 Hz, aromatic 1H), 7.98 (1H, s, CH=N), 7.32 (1H, ddd, J=8.2, 7.5 & 1.7 Hz, aromatic 1H), 6.99 (1H, td, J=6.1 & 7.8 Hz, CH), 4.07 (2H, q, J=7.0 Hz, OCH$_2$), 2.35–2.22 (2H, m, cyclopentyl 2H), 2.07–1.88 (4H, m, cyclopentyl 4H), 1.72–1.57 (2H, m, cyclopentyl 2H) and 1.45 (3H, t, J=7.0 Hz, CH$_3$) ppm.

$^{13}$C NMR (CDCl$_3$, 67.9 MHZ): δ=156.11, 131.00, 128.64, 127.31, 120.50, 119.88, 110.57, 76.64, 63.85 31.38, 25.55 and 14.74 ppm.

Example 45

Synthesis of α-(3-Ethoxy-4-methoxyphenyl)-N-tert-octylnitrone

A solution of 3-ethoxy-4methoxybenzaldehyde, N-tert-octylhydroxylamine and catalytic amount of HCl in methanol was refluxed for 90 hrs with molecular sieves in a soxhlet for waster removal. The title compound was obtained in 60.0% yield as white powder, m.p. 77.5° C. (R$_f$=0.40 on a silica gel plate using hexanes:EtOAc, 3:2, v:v, as an eluant).

Spectroscopic data were as follows:

IR (KBr, cm$^{-1}$): 2975 (CH), 1636 (C=N), 1597 & 1575 (benzene ring), 1279 (Ar—O), 1145 (N—O), and 1039 & 1026 (alkyl-O).

$^1$H NMR (CDCl$_3$, 270 MHZ): δ=8.44 (1H, d, J=2.0 Hz, aromatic 1H), 7.50 (1H, dd, J=8.3 & 2.0 Hz, aromatic 1H), 7.48 (1H, s, CH=N), 6.90 (1H, d, J=8.3 Hz aromatic 1H), 4.20 (2H, q, J=7.0 Hz, OCH$_2$), 3.91 (3H, s, CH$_3$), 1.97 (2H, s, CH$_2$), 1.64 (6H, s, 2CH$_3$), 1.48 (3H, t, J=7.0 Hz, CH$_3$) 0.98 (9H, s, 3CH$_3$), ppm.

$^{13}$C NMR (CDCl$_3$, 67.9 MHZ): δ=150.44, 147.71, 130.41, 124.56, 122.85, 112.22, 110.67, 73.36, 64.23, 55.87, 51.43, 31.63, 30.68, 28.78 and 14.72 ppm.

Example 46

Synthesis of α-(3-Ethoxy-4-methoxyphenyl)-N-(2,4,-dimethyl-2-pentyl)nitrone

The title compound can be prepared according to the procedure described in Example 45 using 3-ethoxy-4-methoxybenzaldehyde and N-2,4,-dimethyl-2-pentylhydroxylamine.

Example 47

Synthesis of α-[4-(4-Fluorobenzyloxy)phenyl]-N-tert-butylnitrone

The title compound was prepared by refluxing a benzene solution of 4-(4-fluorobenzyloxy)benzaldehyde and N-tert-butylhydroxylamine for 21 hours with p-toluenesulfonic acid as a catalyst. The title compound was obtained as a solid in 98.5% yield, m.p. 180.3° C. (R$_f$=0.16 on a silica gel plate using hexanes:EtOAc, 1:1, v/v, as an eluant).

Spectroscopic data were as follows:

IR (KBr, cm$^{-1}$): 2984 (CH), 1607 (C=N & benzene ring), 1509 (benzene ring), 1218 (Ar—O) and 1121 (N—O).

$^1$H NMR (CDCl$_3$, 270 MHz): δ=8.29 (2H, d, J=9.0 Hz, aromatic 2H), 7.47 (1H, s, CH=N), 7.40 (2H, dd, J=8.7 & 5.3 Hz, aromatic 2H), 7.07 (2H, t, J=8.7 Hz, aromatic 2H), 6.99 (2H, d, J=9.0 Hz, aromatic 2H), 5.07 (2H, s, CH$_2$O) and 1.61 (9H, s, C(CH$_3$)$_3$) ppm.

$^{13}$C NMR (CDCl$_3$, 67.9 MHz): δ=162.49 (d, J$_F$=246.5 Hz), 159.69, 132.26, 130.66, 129.37, 129.27, 124.39, 115.47 (d, J$_F$=21.3 Hz), 114.55, 70.12, 69,25, 28.27 ppm.

Example 48

Synthesis of α-(3-Ethoxy-4-methoxyphenyl)-N-cyclobutylnitrone

A solution of 3-ethoxy-4-methoxybenzaldehyde, cyclobutylamine hydrochloride salt, molecular sieves and silica gel in chloroform was refluxed for 20 hours. Filtration and rotary evaporation gave the corresponding imine intermediate which was reduced with NaBH$_4$ in ethanol to give N-cyclobutyl-N-(3-ethoxy-4-methoxybenzyl)amine. This amine intermediate was oxidized with H$_2$O$_2$/Na$_2$WO$_4$ in acetone/water to afford the nitrone product. The title compound was obtained in 19.9% overall yield as cream-colored crystals, m.p. 112.7° C. (R$_f$=0.30 on a silica gel plate using EtOAc as an eluant).

Spectroscopic data were as follows:

IR (KBr, cm$^{-1}$): 2980 (CH), 2935 (CH), 1634 (C=N), 1597 and 1586 (benzene ring), 1265 (Ar—O), 1134 (N—O) and 1047 and 1021 (alkyl-O).

$^1$H NMR (CDCl$_3$, 270 MHz): δ=8.48 (1H, d, J=2.0 Hz, aromatic 1H), 7.42 (1H, dd, J=8.5 and 2.0 Hz, aromatic 1H), 7.30 (1H, s, CH=N), 6.89 (1H, d, J=8.5 Hz, aromatic 1H), 4.53 (1H, quintet, J=8.1 Hz, cyclobutyl CH), 4.19 (2H, q, J=7.0 Hz, OCH$_2$), 3.91 (3H, s, CH$_3$), 2.84–2.68 (2H, m, cyclobutyl 2H), 2.36–2.25 (2H, m, cyclobutyl 2H), 1.91–1.75 (2H, m, cyclobutyl 2H), 1.48 (3H, t, J=7.0, CH$_3$) ppm.

$^{13}$C NMR (CDCl$_3$, 67.9 MHz): δ=150.68, 147.73, 132.30, 123.77, 122.86, 112.11, 110.71, 67.45, 64.18, 55.83, 26.97, 14.69 and 14.15 ppm.

Example 49

Synthesis of α-(3-Ethoxy-4-methoxyphenyl)-N-(4-methylpent-2-yl)nitrone

3-Ethoxy-4-methoxybenzaldehyde (12.0 g, 0.0666 mol) and N-(4-methylpent-2-yl)hydroxylamine (9.36 g, 0.0799 mol) were mixed into benzene (200 mL) with p-toluenesulfonic acid monohydrate (1.0 g, 5.26 mol.). The mixture was refluxed for 16 hours under an argon atmosphere with a Dean-Stark trap to remove the generated water. The solution was rotary evaporated, dissolved in ethyl acetate, washed with 5% aqueous sodium hydroxide solution, dried over magnesium sulfate, filtered and concentrated. The title compound was obtained as a white solid (17.07 g, 91.8% yield), m.p. 87.2° C. (R$_f$=0.31 on a silica gel plate using hexanes;EtOAc, 1:1, v/v, as an eluant). The N-(4-methyl-2-pentyl)hydroxylamine precursor was obtained by sodium cyanoborohydride reduction of 4-methyl-2-pentanone oxime in methanol, with hydrochloric acid catalysis.

Spectroscopic data were as follows:

IR (KBr, cm$^{-1}$): 2962 (CH), 1632 (C=N and benzene ring), 1588 (benzene ring), 1265 (Ar—O) and 1129 (N—O).

$^1$H NMR (CDCl$_3$, 270 MHz): δ=8.44 (1H, d, J=2.0 HZ, aromatic H), 7.45 (1H, dd, J=8.5 and 2.0 Hz, aromatic H), 7.33 (1H, s, CH=N), 6.89 (H, d, J=8.5 Hz, aromatic H), 4.19 (2H, q, J=7.0 Hz, OCH$_2$), 4.07 (1H, m, N(O)CH), 3.91 (3H, s, OCH$_3$), 2.09–1.99 (1H, m, pentyl C$^4$H), 1.66–1.34 (8H, m, CH$_3$ of EtO, pentyl C$^4$H$_3$, and pentyl C$^3$H$_2$), 0.95 (3H, d, J=8.4 Hz, pentyl C$^5$H$_3$), and 0.94 (3H, d, J=8.6 Hz, 4-methyl of pentyl) ppm.

$^{13}$C NMR (CDCl$_3$, 67.9 MHz): δ=150.55, 117.75, 132.59, 123.88, 122.64, 112.12, 110.69, 69.93, 64.19, 55.83, 43.09, 24.74, 22.80, 22.10, 19.64, 14.67 ppm.

Example 50

Synthesis of α-(4-Benzyloxyphenyl)-Nyclooctylnitrone

A solution of 4-benzyloxybenzaldehyde (12.7 g, 0.060 mol), N-cyclooctylhydroxylamine (10.0 g, 0.070 mol) and a catalytic amount of HCl in methanol (300 mL) was refluxed for 56 hours with molecular sieves in a soxhlet for water removal. The reaction mixture was concentrated and dry flash columned on silica with hexanes/ethyl acetate to give the title compound as a pale yellow powder, (9.53 g, 47.0% yield), m.p. 107.5° C. (J$_f$=0.46 on a silica gel plate using hexanes:EtOAc, 1:1, v:v, as an eluant). The N-cyclooctylhydroxylamine precursor was obtained by sodium cyanoborohydride reduction of cyclooctanone oxime in acetic acid/tetrahydrofuran.

Spectroscopic data were as follows:

IR (KBr, cm$^{-1}$): 3061 (CH), 2967 (CH), 1648 (C=N), 1603 (benzene ring), 1579 (benzene ring), 1251 (Ar—O) and 1147 (N—O).

$^1$H NMR (CDCl$_3$, 67.9 MHz): δ=8.22 (2H, d, J=9.0 Hz, aromatic 2H), 7.47–7.29 (6H, m, aromatic 5H & CH=N), 6.99 (2H, d, J=9.0 Hz, aromatic 2H), 5.10 (2H, s, benzyl CH$_2$), 4.08–3.97 (1H, m, N(O)CH), 2.31–2.15 (2H, m, cyclooctyl), 2.10–1.97 (2H, m, cyclooctyl), 1.94–1.76 (2H, m, cyclooctyl), 1.76–1.40 (8H, m, cyclooctyl) ppm.

$^{13}$C NMR (CDCl$_3$, 67.9 MHz): δ=159.80, 136.47, 131.27, 130.34, 128.56, 128.02, 127.44, 124.07, 114.64, 76.73, 69.93, 31.96, 26.54, 26.01, 24.70 ppm.

Examples 51–80

Using the procedures described herein and the appropriate starting materials, the following additional compounds were prepared:

α-(2-ethoxyphenyl)-N-benzylnitrone
α-(3-ethoxy-4-methoxyphenyl)-N-(2,2,4,4-tetramethylpent-3-yl)nitrone
α-(3-ethoxy-4-methoxyphenyl)-N-but-2-ylnitrone
α-(2-ethoxyphenyl)-N-but-2-ylnitrone
α-(3-ethoxy-4-methoxyphenyl)-N-cyclopentylnitrone
α-(3-ethoxy-4-methoxyphenyl)-N-n-propylnitrone
α-(4-benzyloxyphenyl)-N-n-propylnitrone
α-(4-benzyloxyphenyl)-N-isopropylnitrone
α-(3-ethoxy-4-methoxyphenyl)-N-(2-methylbut-2-yl)nitrone
α-(2-ethoxyphenyl)-N-(2-methylbut-2-yl)nitrone
α-(3-ethoxy-4-methoxyphenyl)-N-cyclooctylnitrone
α-(2-ethoxyphenyl)-N-cyclobutylnitrone
α-(4-benzyloxyphenyl)-N-cyclobutylnitrone
α-(4-benzyloxyphenyl)-N-tert-octylnitrone
α-[4-(4-fluorobenzyloxy)phenyl]-N-cyclohexylnitrone
α-(2-ethoxyphenyl)-N-tert-octylnitrone
α-[4-(4-fluorobenzyloxy)phenyl]-N-isopropylnitrone
α-(2-ethoxyphenyl)-N-cyclooctylnitrone
α-(4-benzyloxyphenyl)-N-cyclopropylnitrone
α-(3-ethoxy-4-methoxyphenyl)-N-cyclopropylnitrone
α-(3-ethoxy-4-methoxyphenyl)-N-(3,5-dimethyl-1-adamantyl)nitrone
α-(4-benzyloxyphenyl)-N-1-adamantylnitrone
α-(3-ethoxy-4-methoxyphenyl)-N-(1-methoxy-2-methylprop-2-yl)nitrone
α-(4-benzyloxyphenyl)-N-2-adamantylnitrone
α-(4-ethoxyphenyl)-N-cyclooctylnitrone
α-(4-ethoxyphenyl)-N-1-adamantylnitrone
α-[4-(4-methoxybenzyloxy)phenyl]-N-tert-butylnitrone
α-(3-ethoxy-4-methoxyphenyl)-N-(3-methylbut-1-yl)nitrone
α-(3-ethoxy-4-methoxyphenyl)-N-cyclooctylnitrone, and
α-[4-(4-fluorobenzyloxy)phenyl]-N-cyclopentylnitrone.

Comparative Example 1

Synthesis of α-(2-Methoxyphenyl)-N-tert-butylnitrone

The title compound was prepared according to the procedure described in Example 7 using 2-methoxybenzaldehyde and N-tert-butylhydroxylamine. The title compound was isolated in 82.9% overall yield as white crystals, m.p. 109.1° C. (R$_f$=0.53 on a silica gel plate using ethyl acetate as the eluant).

Spectroscopic data were as follows:

IR (KBr, cm$^{-1}$): 3004.0 (aromatic CH), 2966.0 (CH), 1593.4 (C=N), 1556.1 (benzene ring), 1235.4 (Ar—O), 1125.5 (N—O), and 1017.3 (alkyl-O).

$^1$H NMR (CDCl$_3$, 270 MHz): δ=9.343 (1H, dd, J=7.9 Hz, J=1.7 Hz, aromatic H), 8.025 (1H, s, nitronyl CH), 7.329 (1H, td, J=7.9 Hz, J=1.7 Hz, aromatic H), 6.993 (1H, t, J=7.7 Hz, aromatic H), 6.856 (1H, d, J=8.4 Hz, aromatic H), 3.841 (3H, s, OCH$_3$) and 1.587 (9H, s, 3 CH$_3$).

$^{13}$C NMR (CDCl$_3$, 67.9 MHz): δ=157.452, 131.353, 128.836, 124.535, 120.890, 120.234, 109.739, 70.843, 55.392 and 28.058.

Comparative Example 2

Synthesis of α-(3-Methoxyphenyl)-N-tert-butylnitrone

The title compound was prepared according to the procedure described in Example 11 using 3-methoxybenzaldehyde and N-tert-butylhydroxylamine. The title compound was isolated in 56.5% overall yield as a crystalline solid, m.p. 93.4° C.

Spectroscopic data were as follows:

IR (KBr, cm$^{-1}$): 2977 (CH), 1589 (C=N), 1110 (N—O) and 1035 (C—O).

$^1$H NMR (DMSO-d$_6$, 270 MHz): δ=8.20 (1H, m, phenyl H), 7.84 (1H, s, nitronyl H), 7.78 (1H, d, J=8.0 Hz, phenyl H), 7.33 (1H, t, J=8.0 Hz, phenyl H), 6.98 (1H, dd, J=8.1, 2.5 Hz, phenyl H), 3.77 (3H, s, CH$_3$) and 1.51 (9H, s, 3 CH$_3$).

$^{13}$C NMR (DMSO-d$_6$, 67.9 MHz): δ=159.76, 133.55, 129.80, 129.40, 121.96, 116.41, 113.34, 70.89, 55.35 and 28.04.

Comparative Example 3

Synthesis of α-(4-Ethoxyphenyl)-N-isopropylnitrone

The title compound was prepared according to the procedure described in Example 11 using 4-ethoxybenzaldehyde and N-isopropylhydroxylamine. The title compound was isolated in 41.2% yield as a solid, m.p. 115.1° C.

Spectroscopic data were as follows:

IR (KBr, cm$^{-1}$): 2979.6 (CH), 1597.5 (C=N), 1302.4 (CH$_3$), 1259.2 (C—O—C) and 1169.4 (N—O).

$^1$H NMR (CDCl$_3$, 270 MHz): δ=8.20 (2H, d, J=9.0 Hz, phenyl 2CH), 7.33 (1H, s, nitronyl CH), 6.88 (2H, d, J=9.0 Hz, phenyl 2CH), 4.06 (3H, m, CH$_2$ and CH), 1.46 (6H, m, 2 CH$_3$) and 1.40 (3H, m, CH$_3$).

$^{13}$C NMR (CDCl$_3$, 67.9 MHz): δ=160.6, 131.8, 130.7, 123.8, 114.4, 67.1, 63.4, 20.5 and 14.3.

Comparative Example 4

Synthesis of α-(4-Butoxyphenyl)-N-tert-butylnitrone

The title compound was prepared according to the procedure described in Example 11 using 4-butoxybenzaldehyde and N-tert-butylhydroxylamine. The title compound was isolated in 96% yield (7.18 g) as a solid, m.p. 68.5° C.

Spectroscopic data were as follows:

$^1$H NMR (CDCl$_3$, 270 MHz): δ=8.27 (2H, d, J=8.8, phenyl 2H), 7.45 (1H, s, nitronyl H), 6.91 (2H, d, J=8.8 Hz, phenyl 2H), 4.00 (2 H, t, CH$_2$), 1.60 (9H, s, tert-butyl H), 1.50 (4H, m, 2CH$_2$), 0.97 (3H, t, J=6.7 Hz, CH$_3$).

Comparative Example 5

Synthesis of α-(4-Pentyloxyphenyl)-N-tert-butylnitrone

The title compound was prepared according to the procedure described in Example 2 using 4-hydroxybenzaldehyde, 1-iodopentane and 2-methyl-2-nitropropane. The title compound was isolated in 75% overall yield as a solid, m.p. 43.2° C.

Spectroscopic data were as follows:

IR (KBr, cm$^{-1}$): 3092.7 (CH), 2972.1 (CH), 1604.9 (C=N), 1362.9 (CH$_3$), 1258.8 (C—O—) and 1117.3 (N—O).

$^1$H NMR (CDCl$_3$, 270 MHz): δ=8.24 (2H, d, J=9.1 Hz, phenyl 2H), 7.43 (1H, s, nitronyl H), 6.69 (2H, s, J=9.1 Hz, phenyl 2H), 3.97 (2H, t, J=6.4 Hz, CH$_2$), 1.76 (2H, m, CH$_2$), 1.57 (9H, s, 3 CH$_3$), 1.39 (4H, m, 2, CH$_2$) and 0.90 (3H, t, J=6.9 Hz, CH$_3$).

$^{13}$C NMR (CDCl$_3$, 67.9 MHz) δ=160.8, 130.9, 129.7, 124.0, 114.4, 69.9, 68.0, 28.5, 28.0, 27.8, 22.1 and 13.6.

Comparative Example 6

Synthesis of α-(4-Hexyloxyphenyl)-N-tert-butylnitrone

A solution of 4-hexyloxybenzaldehyde (3.83 g, 18.6 mmol) in 120 mL of benzene was refluxed with N-tert-butylhydroxylamine (3.32 g, 37.2 mmol) for 18 hours. The reaction mixture was then concentrated by rotary evaporation and the resulting residue was purified by silica gel column chromatography using 50:50 ethyl acetate/hexane to afford the title compound (2.88 g, 55.8% yield) as a solid, m.p. 69.0° C.

Spectroscopic data were as follows:

$^1$H NMR (CDCl$_3$, 270 MHz) δ=8.27 (2H, d, J=8.8 Hz, phenyl 2H), 7.45 (1H, s, nitronyl H), 6.91 (2H, d, J=8.8 Hz, phenyl 2H), 4.00 (2H, t, J=6.4 Hz, O—CH$_2$), 1.60 (9H, singlet, tert-butyl H), 1.36 (8H, m, 4 CH$_2$) and 0.90 (3H, t, CH$_3$).

Example I

Electron Spin Resonance (ESR) Study

In this experiment. the ability of α-aryl-N-alkylnitrones of formula I above to trap free radicals is demonstrated using ESR spin trapping techniques. See, for example, K. R. Maples et al., "In Vivo Detection of Free Radical Metabolites"; *Free Radicals in Synthesis and Biology* (F. Minisci, ed.) pp. 423–436 (Kluwer Academic Publishers, Boston, 1989); and J. A. DeGray et al., "Biological Spin Trapping", *Electron Spin Resonance* 14:246–300 (1994). A t-butyl hydroperoxide/ferrous iron free radical generating system was used in this experiment. This free radical generating system produces t-butyl-alkoxyl radicals, t-butyl-peroxyl radicals, and methyl radicals. If the α-aryl-N-alkylnitrones of this invention are capable of trapping any of these radicals to form a stable radical adduct, such radical adducts should be detectable by ESR spectroscopy.

To 490 μl of a 100 mM solution of α-(2-ethoxyphenyl)-N-tert-butylnitrone in water was added 5 μl of 100 mM ferrous sulfate. The reaction was initiated by the addition of 5 μl of 100 mM t-butyl hydroperoxide. The final concentrations of reagents are 1 mM ferrous iron, 1 mM t-butyl hydroperoxide and 98 mM of the nitrone compound in water. Once mixed, the solution was quickly transferred into a quartz flat cell and this cell was placed in the cavity of a Bruker ESP 300 ESR spectrometer, and scanned within 5 minutes of mixing. ESR spectrometer settings were: 3480 G center field, 200 G field width, 480 seconds sweep time, 9.76 GHz frequency, 10 dB power, $1.6 \times 10^5$ receiver gain, 0.200 G modulation amplitude, 0.320 second time constant, and 270° phase. The resulting ESR spectrum, as shown in FIG. 1, consisted of primarily one species, characterized as a 16.8 G (1:1:1) triplet of 4.3 G (1:1) doublets, representing $a_N$ and $a_H$, respectively. This species is believed to be the methyl radical adduct of α-(2-ethoxyphenyl)-N-tert-butylnitrone. Thus, the ESR spectrum shown in FIG. 1 demonstrates that the α-aryl-N-alkylnitrones of formula I are effective at trapping free radicals and that such compounds can be used as analytical reagents for ESR applications.

Example II

Inhibition of Aβ Beta-Pleated Sheet Formation

The deposition of amyloid β-peptide (Aβ) is associated with the development of Alzheimer's disease. See, for example, G. G. Glenner et al. (1984) *Biochem. Biophys. Res. Commun.*, 120:885–890; and R. E. Tanzi (1989) *Ann. Med.*, 21:91–94. Accordingly, compounds which effectively disrupt the formation of Aβ(1-40) or Aβ(1-42) beta-pleated sheets are potentially useful for preventing and/or reversing such amyloid deposits. Thioflavin T (ThT) is known to rapidly associate with bet-pleated sheets, particularly the aggregated fibrils of synthetic Aβ(1-42). This association gives rise to an excitation maximum at 440 nm and to an emission at 490 nm. In this experiment, the ability of certain α-aryl-N-alkylnitrones of formula I above to inhibit the association of ThT with synthetic Aβ(1-42) is demonstrated by measuring changes in fluorescence.

The experiments were performed using a CytoFluor II fluorescence plate reader having the following parameters:
Filters
Excitation 440 nm/20
Emission 490 nm/40
Gain
75
Cycle to Cycle Time
30 min
Run Time
720 min (24 cycles) or dependent on experimental design
Plate
96 well Into each well was aliquoted 95 μl of ThT (3 μM) prepared in PBS (pH 6.0), 2 μL of the compound to be tested (10 μM) prepared with 0.05% of methylcellulose in PBS (pH 6.0), and 3 μL of Aβ(1-42)(3 μg) prepared with dH$_2$O. The fluorescence measurement began when the Aβ(1-42) was added and continued for a total of 12 hours. The percent inhibition of beta-pleated sheet formation was calculated from the relative fluorescence unit difference between aggregation in the presence and in the absence of the test compounds. Inhibition of Aβ(1-42) beta-pleated sheet formation by at least 30% compared to the controls is considered significant in this test. The results of these in vitro tests are described below.

Example III

Protection Against Aβ(25-35)-Induced Neuronal Cell Loss

Patients with Alzheimer's disease are known to suffer a progressive loss of neuronal cells. See, for example, P. J. Whitehause et al., (1982) *Science*, 215:1237–1239. In this experiment, the ability of certain α-aryl-N-alkylnitrones of formula I above to protect against Aβ(25-35)-induced neuronal cell loss is demonstrated. Sprague Dawley rat hippocampus of 18-day-gestation embryos was excised and then dissociated by trituration to prepare primary neuronal cultures. Cells ($3 \times 10^5$) were plated on 35 mm poly-D-lysine-coated plates containing Eagle's minimum essential medium supplemented with 10% fetal bovine serum. After 3–5 hours, the original medium was removed and replaced with 1 mL of fresh medium. Cultures were maintained at 37° C. in a 5% CO$_2$/95% air humidified incubator. Glial growth is observed as a monolayer under neurons.

To the cells (7 DIV) was added 30 μM of Aβ(25-35) dissolved in dH$_2$O (stored at −20° C.) and 100 μM of the test compound in 1% methylcellulose. Controls were also conducted without the test compound. The percentage of morphologically viable neurons was determined by counting the number of viable neurons after 96 hours treatment (three regions/well, n=6 wells). Inhibition of Aβ(25-35)-induced neuronal cell loss by at least 30% compared to the controls is considered significant in this test. The results of these in vitro tests are described below.

Example IV

Reduction of β-Amyloid-Induced Increased Release of Interleukin-1β and Tumor Necrosis Factor-α

In this experiment, the ability of certain α-aryl-N-alkylnitrones of formula I above to reduce the β-amyloid-induced increased release over LPS alone of interleukin-1β (IL-1β) and tumor necrosis factor-α (TNFα) is demonstrated. THP-1 cells, a human monocyte cell line from American Type Culture Collection, were grown in RPMI-1640 medium plus 10% fetal bovine serum (FBS, not heat-inactivated) in T-flasks. The medium was changed every two days by spinning down the cells (800 rpm, 5 minutes) and adding the same fresh medium. Alternatively, the cultures were maintained by supplementation with fresh medium. The cultures were maintained at a cell concentration ranging from between $1 \times 10^5$ and $1 \times 10^6$ cells/mL. Because sera may contain unknown factors which can affect macrophage/monocyte IL-1 production, the FBS was reduced to 5% for 24 hours. The FBS was further reduced to 2% over two days prior to starting each experiment. The cells were collected by centrifugation and resuspended in media containing 2% FBS. Cell numbers were calculated and cells were plated on 24-well plates ($3 \times 10^5$ cells/0.6 mL/well). Cells were then treated with LPS (0.5 μg/ml or 0–10 μg/ml for LPS dose-response experiments) alone or in combination with Aβ peptides (5 μM or 0.05–5 μM for dose-response experiments). When determining the effect of the test compounds on IL-1β and TNFα release, 100 μM of the test compound was added with the LPS and Aβ(25-35) and this mixture was incubated for 48 hours prior to performing ELISA.

IL-1β and TNFα secretions into medium by LPS-stimulated THP-1 cells, in the presence or absence of amyloid peptides and a test compound, were assayed with a commercially available ELISA kit (R & D Systems). Briefly, a microtiter plate coated with a murine monoclonal antibody to human IL-1β or TNFα was supplied by the manufacturer. Standards and samples were pipetted into the wells and any IL-1β or TNFα present was bound by the immobilized antibody. Unbound proteins were washed away and a horseradish peroxidase-linked polyclonal antibody specific for IL-1β or TNFα was added to the wells to "sandwich" the IL-1β and TNFα bound in the initial step. After washing to remove any unbound antibody-enzyme reagent, a substrate solution (1:1 hydrogen peroxide:tetramethylbenzidine, v/v) was added to the wells and color developed in proportion to the amount of IL-1β or TNFα bound in the initial step. Color development was stopped with 2 N sulfuric acid and the optical density of the standard and the test samples was measured at 450 nm. The amounts of IL-1β or TNFα present in the samples were calculated based upon a standard curve. Assays were run in quadruplicate wells. Inhibition of β-amyloid-induced increase release of interleukin-1β or tumor necrosis factor by at least 30% compared to controls is considered significant in these tests. The results of these in vitro tests are described below.

Example V

Protection Against IL-1β and IFNγ-Induced Toxicity

In this experiment, the ability of certain α-aryl-N-alkylnitrones of formula I above to reduce the IL-1β and IFNγ-induced neuronal toxicity in mixed rat hippocampal neuronal cultures is demonstrated. Rat hippocampus of 18-day-gestation embryos were dissected free and incubated in HBSS containing 0.1% trypsin at 37° C. for 30 minutes. Tissue was then suspended in plating medium consisting of Eagle's minimum essential medium supplemented with 2 mM L-glutamine, 14.75 mM KCl, 1 mM pyruvic acid, 10% fetal bovine serum and 100 units/mL penicillin/100 μg/mL streptomycin. After trituration through a flame-polished Pasteur pipette, cells were diluted in additional plating medium, counted and seeded at a density of $3.5 \times 10^5$/mL/well on Falcon 6-well plates which were precoated with 20 μg/mL poly-D-lysine for 2–3 hours at room temperature, and washed twice with HBSS. After 3–5 hours, the original medium was removed and replaced with 1 mL of fresh medium. Cultures were maintained at 37° C. in a 5% $CO_2$/95% air humidified incubator for 12 days.

12 DIV hippocampal cultures which contain neurons and astrocytes were used to perform the experiment. In each well was added 200 U/mL of recombinant mouse IL-1β (Genzyme) and 1,000 U/mL of IFNγ (Genzyme). 10 μL of the test compound (100 μM final concentration) in 1% methyl cellulose was added immediately to each well. To control wells were added only 1% methyl cellulose. Dexamethasone (30 μM) was used as a positive control. Cultures were incubated at 37° C. in a humidified atmosphere containing 5% $CO_2$ for 48 or 96 hours. Neuronal injury was estimated in all experiments by examination of cultures with phase-contrast microscopy and was quantified by measurement of cytosolic lactate dehydrogenase (LDH) release into the culture medium.

Release of LDH into the bathing medium was estimated from the conversion of NAD to NADH, after lactate addition, and was measured spectrophotometrically from the rate of decrease in 340 nm absorbance. LDH activity is defined as that amount of enzyme that catalyzed the formation of one micromole of NADH per minute under the conditions of the assay procedure. To a 96-well plate, 0.05 mL medium collected from each sample was added to and then mixed with 0.10 mL reagent from LD-L 20 kit (Sigma). The plate was immediately placed into the SpectraMax 340 plate reader to read at 340 nm wavelength at 25° C. for 3 minutes at 30 second intervals. Reduction of neuronal injury by at least 30% compared to controls is considered significant in this test. The results of this in vitro test are described below.

In vitro Test Results

Certain of the compounds prepared in the above examples were tested in at least one of the above described in vitro tests. The compounds of this invention either inhibited Aβ(1-42) beta-pleated sheet formation and/or Aβ(25-35)-induced neuronal cell loss and/or β-amyloid-induced increase release of interleukin-1β and/or tumor necrosis factor and/or IL-1β/IFN$_γ$-induced toxicity by at least 30% compared to the controls or are expected to be effective in at least one of these in vitro assays upon further testing. In contrast, the compounds of Comparative Examples 1–6 failed to inhibit Aβ(1-42) beta-pleated sheet formation and/or Aβ(25-35)-induced neuronal cell loss and/or β-amyloid-induced increase release of interleukin-1β and/or tumor necrosis factor and/or IL-1β/IFN$_γ$-induced toxicity by at least 30% compared to the controls.

Example VI

Reduction of Cognitive Defects Due to Aβ-Peptide/Ibotenate

In this experiment, the ability of certain α-aryl-N-alkylnitrones of formula I above to reduce the in vivo impairment of animals treated with ibotenate and Aβ(25-35) is demonstrated. The procedures employed in this example are similar to those described in Dornan et al., *NeuroReport* 5, 165–168 (1993). Male Sprague-Dawley rats (200–300 g) were weighed and given 10 mg/kg of α-(2-ethoxyphenyl)-N-tert-butylnitrone or 1% methylcellulose by oral gavage. One hour later, the rats were stereotaxically injected into the CA1 region of their hippocampus with 8 nmol of Aβ(25-35) and 6 nmol of ibotenate per side (coordinates from bregma −3.6=AP, ±2.2=ML, −3.0=DV from the top of the dura). Controls were injected with PBS (pH 7.4). All injections were 1.5 μL in volume. The animals receiving PBS were orally dosed with 1% methylcellulose. Oral dosing continued daily until the end of the Morris water maze testing.

Nine to eleven days following injection, animals were tested in a Morris water maze task to measure spatial memory and learning. Animals were given three days of testing with four to six trials per day. The last trial on the fourth day was a probe trial where the platform was removed and time in quadrant and annulae crossings were determined. Following the behavioral testing, animals were perfused with 10% neutral formalin. The brain was post-fixed for 1 week in 10% formalin and then sliced for histological evaluation. Image analysis of cresyl violet staining was used to compare the neuronal loss (lesion volume) in the hippocampus between groups. The data show that α-(2-ethoxyphenyl)-N-tert-butylnitrone reduced the Aβ peptide/ibotenate-induced learning deficit.

Example VII

Reduction of Cognitive Deficits in Autoimmune Mice

In this experiment, the ability of certain α-aryl-N-alkylnitrones of formula I above to reduce cognitive deficits in autoimmune strains of mice is demonstrated. MRL/MpJfas$^{lpr}$ ("mutant mice" or "Fas$^{lpr}$") strains of mice have been described as useful models of Lupus due to their autoimmune lymphoproliferative pathology. In particular, the mutant mice show a cognitive deficit at approximately four months of age, which is not observed at two months of age. See, for example, Forster et al., 1988, *Behav. Neural Biology*, 49, 139–151.

In the experiment, male MRL/MpJ Fas$^{lPr}$ and normal MRL/MpJ++ mice of 8 weeks of age were weighed and administered 100 mg/kg of the test compound (either α-(2-ethoxyphenyl)-N-tert-butylnitrone or α-(4-ethoxyphenyl)-N-cyclohexylnitrone) or 1% methylcellulose vehicle by oral gavage daily for 8 to 9 weeks. At 4 months of age, the mice were tested for avoidance, discrimination, session criteria and acquisition in a one day T-maze task with a maximum of 25 trials. Criteria was met with four of five trials correct with the last two correct trials being consecutive in avoidance and discrimination. The Fas$^{lpr}$ mice showed a deficit in both avoidance and acquisition compared to the normal mice which received the 1% methylcellulose. In contrast, the Fas$^{lpr}$ mice treated with the test compounds of this invention had reduced acquisition values and acquired avoidance skills earlier than untreated mutant mice (i.e., similar to the normal controls). These results demonstrate that α-aryl-N-alkylnitrones of formula I above reduced the cognitive deficits of the autoimmune strains of mice.

Example VIII

Prevention of MBP-Induced Experimental Allergic Encephalomyelitis

Multiple sclerosis (MS) is a chronic inflammatory CNS disorder caused by demyelination in the brain and spinal cord. The disease is characterized by progressive CNS dysfunction, including muscular weakness, tremor, incontinence, ocular disturbances, and mental dysfunction, with remissions and exacerbations.

Experimental allergic encephalomyelitis (EAE) induced by injection of guinea pig myelin basic protein (MBP) or MBP peptide fragments is reported to be a useful model for MS. See, for example, D. E. McFarlin et al., "Recurrent Experimental Allergic Encephalomyelitis in the Lewis Rat," The Journal of Immnunology, 113(2): 712–715 (1974). In this experiment, the ability of certain α-aryl-N-alkylnitrones of formula I above to prevent MBP-induced EAE is demonstrated.

Female, Lewis rats of 8 weeks of age (180–250 g) were weighed and then given two intradermal injections (0.1 mL each) of 0.4 mg of M. tuberculin in 0.1 mL incomplete Freunds adjuvant and 50 mg of myelin basic protein in 0.1 mL of saline into the base of the tail. Animals were weighed daily and given a clinical score beginning on Day 8, post inoculation, according to the following criteria:

0.0=No illness
0.5=Tip of tail flaccid
1.0=Entire tail flaccid
1.5=Hind limb weakness
2.0=Hind limb paralysis
2.5=Hind limb paralysis and front limb weakness
3.0=Hind and front limb paralysis
4.0=Moribund state or death On day 3, post-inoculation animals were administered b.i.d either a test compound (100 mg/kg) or 1% methylcellulose vehicle by oral gavage up to and including day 16. The results demonstrate that the compounds of Examples 3, 11, 17, 22, 41, 42 and 45 reduced the CNS inflammatory deficit in acute EAE animals. At the doses tested, the compounds of Examples 4, 5, 7, 10, 15 and 29 did not significantly reduce the CNS inflammatory deficit.

From the foregoing description, various modifications and changes in the compositions and methods of this invention will occur to those skilled in the art. All such modifications coming within the scope of the appended claims are intended to be included therein.

What is claimed is:

1. A method for treating a patient with a neurodegenerative disease selected from Alzheimer's disease, Parkinson's disease and HIV dementia which method comprises administering to said patient a pharmaceutical composition comprising a pharmaceutically acceptable carrier and an effective neurodegenerative disease-treating amount of a compound of formula I:

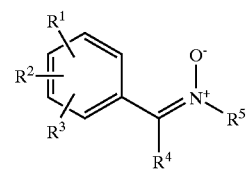

wherein
$R^1$ is selected from the group consisting of alkoxy, alkaryloxy, alkcycloalkoxy, aryloxy, and cycloalkoxy;
$R^2$ is selected from the group consisting of hydrogen, alkoxy, alkcycloalkoxy, cycloalkoxy and halogen, or when $R^1$ and $R^2$ are attached to adjacent carbon atoms, $R^1$ and $R^2$ may be joined together to form an alkylenedioxy group;
$R^3$ is selected from the group consisting of hydrogen, alkoxy, alkcycloalkoxy, cycloalkoxy and halogen;
$R^4$ is selected from the group consisting of hydrogen and alkyl;
$R^5$ is selected from the group consisting of alkyl having at least 3 carbon atoms, substituted alkyl having at least 3 carbon atoms and cycloalkyl;
provided that:
(i) when $R^2$ and $R^3$ are independently hydrogen or methoxy, $R^1$ is not methoxy;
(ii) when $R^2$, $R^3$ and $R^4$ are hydrogen and $R^5$ is tert-butyl, then $R^1$ is not 4-n-butoxy, 4-n-pentyloxy or 4-n-hexyloxy;
(iii) when $R^2$, $R^3$ and $R^4$ are hydrogen and $R^5$ is isopropyl, then $R^1$ is not 4-ethoxy;
(iv) when $R^1$ and $R^2$ are joined together to form a 3,4-methylenedioxy group and $R^3$ and $R^4$ are hydrogen, then $R^5$ is not isopropyl or tert-butyl;
(v) when $R^2$, $R^3$ and $R^4$ are hydrogen and $R^5$ is 1-hydroxy-2-methylprop-2-yl, then $R^1$ is not 2-ethoxy;
(vi) when $R^1$ is 4-methoxy, $R^2$ is 3-ethoxy, and $R^3$ and $R^4$ are hydrogen, then $R^5$ is not 2,2-dimethylbut-3-yl or 1-hydroxy-2-methylprop-2-yl; and
(vii) when $R^3$ and $R^4$ are hydrogen and $R^5$ is tert-butyl, then $R^1$ is not 4-methoxy when $R^2$ is 2-fluoro, and $R^1$ is not 2-methoxy when $R^2$ is 4-fluoro.

2. The method according to claim 1 wherein the neurodegenerative disease is Alzheimer's disease.

3. The method according to claim 1 wherein the neurodegenerative disease is Parkinson's disease.

4. The method according to claim 1 wherein the neurodegenerative disease is HIV dementia.

5. A method for treating a patient with an autoimmune disease selected from systemic lupus and multiple sclerosis, which method comprises administering to said patient a pharmaceutical composition comprising a pharmaceutically acceptable carrier and an effective autoimmune disease-treating amount of a compound of formula I:

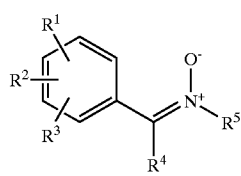

wherein

R¹ is selected from the group consisting of alkoxy, alkaryloxy, alkcycloalkoxy, aryloxy, and cycloalkoxy;

R² is selected from the group consisting of hydrogen, alkoxy, alkcycloalkoxy, cycloalkoxy and halogen, or when R¹ and R² are attached to adjacent carbon atoms, R¹ and R² may be joined together to form an alkylenedioxy group;

R³ is selected from the group consisting of hydrogen, alkoxy, alkcycloalkoxy, cycloalkoxy and halogen;

R⁴ is selected from the group consisting of hydrogen and alkyl;

R⁵ is selected from the group consisting of alkyl having at least 3 carbon atoms, substituted alkyl having at least 3 carbon atoms and cycloalkyl;

provided that:
(i) when R² and R³ are independently hydrogen or methoxy, R¹ is not methoxy;
(ii) when R², R³ and R⁴ are hydrogen and R⁵ is tert-butyl, then R¹ is not 4-n-butoxy, 4-n-pentyloxy or 4-n-hexyloxy;
(iii) when R², R³ and R⁴ are hydrogen and R⁵ is isopropyl, then R¹ is not 4-ethoxy;
(iv) when R¹ and R² are joined together to form a 3,4-methylenedioxy group and R³ and R⁴ are hydrogen, then R⁵ is not isopropyl or tert-butyl;
(v) when R², R³ and R⁴ are hydrogen and R⁵ is 1-hydroxy-2-methylprop-2-yl, then R¹ is not 2-ethoxy;
(vi) when R¹ is 4-methoxy, R² is 3-ethoxy, and R³ and R⁴ are hydrogen, then R⁵ is not 2,2-dimethylbut-3-yl or 1-hydroxy-2-methylprop-2-yl; and
(vii) when R³ and R⁴ are hydrogen and R⁵ is tert-butyl, then R¹ is not 4-methoxy when R² is 2-fluoro, and R¹ is not 2-methoxy when R² is 4-fluoro.

6. The method according to claim 5 wherein the autoimmune disease is systemic lupus.

7. The method according to claim 5 wherein the autoimmune disease is multiple sclerosis.

8. A method for treating a patient with an inflammatory disease selected from the group consisting of systemic lupus, multiple sclerosis, rheumatoid arthritis, septic shock, erythema nodosum leprosy, septicemia, uveitis, adult respiratory distress syndrome, and inflammatory bowel disease, which method comprises administering to said patient a pharmaceutical composition comprising a pharmaceutically acceptable carrier and an effective inflammatory disease-treating amount of a compound of formula I:

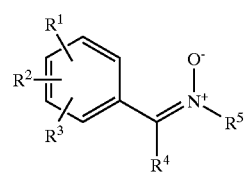

wherein

R¹ is selected from the group consisting of alkoxy, alkaryloxy, alkcycloalkoxy, aryloxy, and cycloalkoxy;

R² is selected from the group consisting of hydrogen, alkoxy, alkcycloalkoxy, cycloalkoxy and halogen, or when R¹ and R² are attached to adjacent carbon atoms, R¹ and R² may be joined together to form an alkylenedioxy group;

R³ is selected from the group consisting of hydrogen, alkoxy, alkcycloalkoxy, cycloalkoxy and halogen;

R⁴ is selected from the group consisting of hydrogen and alkyl;

R⁵ is selected from the group consisting of alkyl having at least 3 carbon atoms, substituted alkyl having at least 3 carbon atoms and cycloalkyl;

provided that:
(i) when R² and R³ are independently hydrogen or methoxy, R¹ is not methoxy;
(ii) when R², R³ and R⁴ are hydrogen and R⁵ is tert-butyl, then R¹ is not 4-n-butoxy, 4-n-pentyloxy or 4-n-hexyloxy;
(iii) when R², R³ and R⁴ are hydrogen and R⁵ is isopropyl, then R¹ is not 4-ethoxy;
(iv) when R¹ and R² are joined together to form a 3,4-methylenedioxy group and R³ and R⁴ are hydrogen, then R⁵ is not isopropyl or tert-butyl;
(v) when R², R³ and R⁴ are hydrogen and R⁵ is 1-hydroxy-2-methylprop-2-yl, then R¹ is not 2-ethoxy;
(vi) when R¹ is 4-methoxy, R² is 3-ethoxy, and R³ and R⁴ are hydrogen, then R⁵ is not 2,2-dimethylbut-3-yl or 1-hydroxy-2-methylprop-2-yl; and
(vii) when R³ and R⁴ are hydrogen and R⁵ is tert-butyl, then R¹ is not 4-methoxy when R² is 2-fluoro, and R¹ is not 2-methoxy when R² is 4-fluoro.

9. The method according to claim 8 wherein the inflammatory disease is rheumatoid arthritis.

10. The method according to claim 8 wherein the inflammatory disease is septic shock.

11. The method according to claim 8 the inflammatory disease is erythema nodosum leprosy.

12. The method according to claim 8 wherein the inflammatory disease is septicemia.

13. The method according to claim 8 the inflammatory disease is uveitis.

14. The method according to claim 8 wherein the inflammatory disease is adult respiratory distress syndrome.

15. The method according to claim 8 wherein the inflammatory disease is inflammatory bowel disease.

16. A method for treating a patient with a disease characterized by the release of cytokines, which method comprises administering to said patient a pharmaceutical composition comprising a pharmaceutically acceptable carrier and an effective cytokine release-inhibiting amount of a compound of formula I:

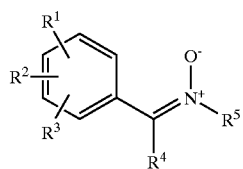

wherein
- $R^1$ is selected from the group consisting of alkoxy, alkaryloxy, alkcycloalkoxy, aryloxy, and cycloalkoxy;
- $R^2$ is selected from the group consisting of hydrogen, alkoxy, alkcycloalkoxy, cycloalkoxy and halogen, or when $R^1$ and $R^2$ are attached to adjacent carbon atoms, $R^1$ and $R^2$ may be joined together to form an alkylenedioxy group;
- $R^3$ is selected from the group consisting of hydrogen, alkoxy, alkcycloalkoxy, cycloalkoxy and halogen;
- $R^4$ is selected from the group consisting of hydrogen and alkyl;
- $R^5$ is selected from the group consisting of alkyl having at least 3 carbon atoms, substituted alkyl having at least 3 carbon atoms and cycloalkyl;

provided that:
- (i) when $R^2$ and $R^3$ are independently hydrogen or methoxy, $R^1$ is not methoxy;
- (ii) when $R^2$, $R^3$ and $R^4$ are hydrogen and $R^5$ is tert-butyl, then $R^1$ is not 4-n-butoxy, 4-n-pentyloxy or 4-n-hexyloxy;
- (iii) when $R^2$, $R^3$ and $R^4$ are hydrogen and $R^5$ is isopropyl, then $R^1$ is not 4-ethoxy;
- (iv) when $R^1$ and $R^2$ are joined together to form a 3,4-methylenedioxy group and $R^3$ and $R^4$ are hydrogen, then $R^5$ is not isopropyl or tert-butyl;
- (v) when $R^2$, $R^3$ and $R^4$ are hydrogen and $R^5$ is 1-hydroxy-2-methylprop-2-yl, then $R^1$ is not 2-ethoxy;
- (vi) when $R^1$ is 4-methoxy, $R^2$ is 3-ethoxy, and $R^3$ and $R^4$ are hydrogen, then $R^5$ is not 2,2-dimethylbut-3-yl or 1-hydroxy-2-methylprop-2-yl; and
- (vii) when $R^3$ and $R^4$ are hydrogen and $R^5$ is tert-butyl, then $R^1$ is not 4-methoxy when $R^2$ is 2-fluoro, and $R^1$ is not 2-methoxy when $R^2$ is 4-fluoro.

17. The method of claim 16 wherein the cytokine is selected from the group consisting of IL-1β, IL-6 and TNF-α.

* * * * *